(12) United States Patent
Kreel et al.

(10) Patent No.: US 12,168,787 B2
(45) Date of Patent: *Dec. 17, 2024

(54) PROCESS OF EXTRACTING OIL FROM THIN STILLAGE

(71) Applicant: Novozymes A/S, Bagsvaerd (DK)

(72) Inventors: Nathaniel Edward Kreel, Louisburg, NC (US); Joseph Mark Jump, Raleigh, NC (US); Bernardo Vidal, Jr., Wake Forest, NC (US); Chee-Leong Soong, Raleigh, NC (US); Madison Roberts, Raleigh, NC (US); Melissa Carrie Hooss, Franklinton, NC (US); Xinyu Shen, Wake Forest, NC (US)

(73) Assignee: Novozymes A/S, Bagsvaerd (DK)

( * ) Notice: Subject to any disclaimer, the term of this patent is extended or adjusted under 35 U.S.C. 154(b) by 29 days.

This patent is subject to a terminal disclaimer.

(21) Appl. No.: 18/313,955

(22) Filed: May 8, 2023

(65) Prior Publication Data

US 2023/0340432 A1 Oct. 26, 2023

Related U.S. Application Data

(63) Continuation of application No. 17/306,001, filed on May 3, 2021, now Pat. No. 11,674,127, which is a continuation of application No. 16/787,203, filed on Feb. 11, 2020, now Pat. No. 11,028,378, which is a continuation of application No. 16/062,519, filed as application No. PCT/US2016/067080 on Dec. 16, 2016, now Pat. No. 10,597,645.

(60) Provisional application No. 62/271,182, filed on Dec. 22, 2015, provisional application No. 62/271,063, filed on Dec. 22, 2015, provisional application No. 62/324,107, filed on Apr. 18, 2016, provisional application No. 62/430,695, filed on Dec. 6, 2016.

(51) Int. Cl.
| | | |
|---|---|---|
| *C12N 9/14* | (2006.01) | |
| *C12N 9/16* | (2006.01) | |
| *C12N 9/20* | (2006.01) | |
| *C12N 9/26* | (2006.01) | |
| *C12N 9/28* | (2006.01) | |
| *C12N 9/34* | (2006.01) | |
| *C12N 9/42* | (2006.01) | |
| *C12N 9/44* | (2006.01) | |
| *C12N 9/50* | (2006.01) | |
| *C12P 7/06* | (2006.01) | |
| *C12P 7/64* | (2022.01) | |
| *C12P 19/14* | (2006.01) | |

(52) U.S. Cl.
CPC ............ *C12N 9/14* (2013.01); *C12N 9/16* (2013.01); *C12N 9/20* (2013.01); *C12N 9/2414* (2013.01); *C12N 9/2417* (2013.01); *C12N 9/2428* (2013.01); *C12N 9/2437* (2013.01); *C12N 9/2457* (2013.01); *C12N 9/50* (2013.01); *C12P 7/06* (2013.01); *C12P 19/14* (2013.01); *C12Y 301/03008* (2013.01); *C12Y 301/04* (2013.01); *C12Y 301/04011* (2013.01); *C12Y 302/01001* (2013.01); *C12Y 302/01003* (2013.01); *C12Y 302/01004* (2013.01); *C12Y 302/01008* (2013.01); *C12Y 302/01041* (2013.01); *C12Y 304/21062* (2013.01); *C12Y 304/23023* (2013.01); *C12Y 304/24039* (2013.01); *C12P 7/64* (2013.01); *Y02E 50/10* (2013.01)

(58) Field of Classification Search
None
See application file for complete search history.

(56) References Cited

U.S. PATENT DOCUMENTS

| | | | | |
|---|---|---|---|---|
| 5,800,849 | A * | 9/1998 | Budtz | A23C 19/0326 426/38 |
| 8,008,517 | B2 | 8/2011 | Cantrell et al. | |
| 8,535,927 | B1 | 9/2013 | Jones et al. | |
| 9,279,110 | B2 | 3/2016 | Tang et al. | |

(Continued)

FOREIGN PATENT DOCUMENTS

| | | |
|---|---|---|
| CN | 103608460 A | 2/2014 |
| CN | 104838009 A | 8/2015 |

(Continued)

OTHER PUBLICATIONS

Devos et al., Proteins: Structure, Function, and Genetics 41, 2000, 98-107, 41.

(Continued)

*Primary Examiner* — Suzanne M Noakes
*Assistant Examiner* — Jae W Lee
(74) *Attorney, Agent, or Firm* — Kelly K. Reynolds

(57) ABSTRACT

A process of recovering oil, comprising (a) converting a starch-containing material into dextrins with an alpha-amylase; (b) saccharifying the dextrins using a carbohydrate source generating enzyme to form a sugar; (c) fermenting the sugar in a fermentation medium into a fermentation product using a fermenting organism; (d) recovering the fermentation product to form a whole stillage; (e) separating the whole stillage into thin stillage and wet cake; (e') optionally concentrating the thin stillage into syrup; (f) recovering oil from the thin stillage and/or optionally the syrup, wherein a protease and a phospholipase are present and/or added during steps (a) to (c). Use of a protease and a phospholipase for increasing oil recovery yields from thin stillage and/or syrup in a fermentation product production process.

12 Claims, 1 Drawing Sheet
Specification includes a Sequence Listing.

(56) References Cited

U.S. PATENT DOCUMENTS

| | | | |
|---|---|---|---|
| 9,528,128 | B2 | 12/2016 | Hansen |
| 9,816,112 | B2 | 11/2017 | Deinhammer |
| 10,597,645 | B2 | 3/2020 | Jump et al. |
| 11,028,378 | B2 | 6/2021 | Jump et al. |
| 2004/0063184 | A1 | 4/2004 | Grichko |

FOREIGN PATENT DOCUMENTS

| | | | |
|---|---|---|---|
| EP | 1905821 | A1 | 4/2008 |
| WO | 2005079193 | A2 | 9/2005 |
| WO | 2011126897 | A2 | 10/2011 |
| WO | 2014074452 | A1 | 5/2014 |
| WO | 2014090161 | A1 | 6/2014 |
| WO | 2014209789 | A1 | 12/2014 |
| WO | 2015116395 | A1 | 8/2015 |
| WO | 2015173426 | A1 | 11/2015 |

OTHER PUBLICATIONS

Majoni et al., Majoni 2011 JAOCS 88(4) 523-532 Danisco IPR, J Am Oil Chem Soc, 2011, 523-532, 88(4).

Wang et al., J Agric Food Chem, 2009, 2302-2307, 57(6).

\* cited by examiner

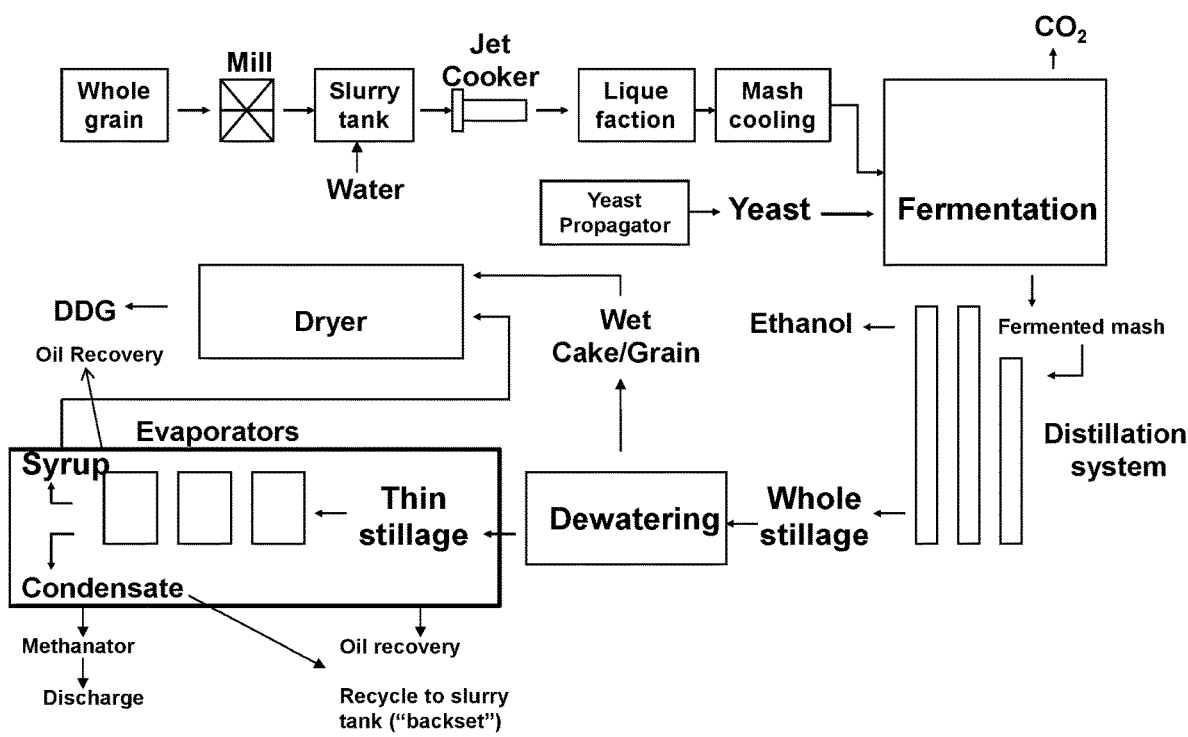

SEQUENCE LISTING

```
Sequence total quantity: 17
SEQ ID NO: 1            moltype = AA  length = 515
FEATURE                 Location/Qualifiers
REGION                  1..515
                        note = mat_peptide
source                  1..515
                        mol_type = protein
                        organism = Bacillus stearothermophilus
SEQUENCE: 1
AAPFNGTMMQ YFEWYLPDDG TLWTKVANEA NNLSSLGITA LWLPPAYKGT SRSDVGYGVY   60
DLYDLGEFNQ KGTVRTKYGT KAQYLQAIQA AHAAGMQVYA DVVFDHKGGA DGTEWVDAVE  120
VNPSDRNQEI SGTYQIQAWT KFDPPGRGNT YSSFKWRWYH FDGVDWDESR KLSRIYKFRG  180
IGKAWDWEVD TENGNYDYLM YADLDMDHPE VVTELKNWGK WYVNTTNIDG FRLDAVKHIK  240
FSFFPDWLSY VRSQTGKPLF TVGEYWSYDI NKLHNYITKT NGTMSLFDAP LHNKFYTASK  300
SGGAFDMRTL MTNTLMKDQP TLAVTFVDNH DTEPGQALQS WVDPWFKPLA YAFILTRQEG  360
YPCVFYGDYY GIPQYNIPSL KSKIDPLLIA RRDYAYGTQH DYLDHSDIIG WTREGVTEKP  420
GSGLAALITD GPGGSKWMYV GKQHAGKVFY DLTGNRSDTV TINSDGWGEF KVNGGSVSVW  480
VPRKTTVSTI ARPITTRPWT GEFVRWTEPR LVAWP                             515
```

```
SEQ ID NO: 2               moltype = DNA   length = 1068
FEATURE                    Location/Qualifiers
sig_peptide                1..57
misc_feature               58..534
mat_peptide                535..1068
source                     1..1068
                           mol_type = genomic DNA
                           organism = Thermoascus aurantiacus
CDS                        1..1065
SEQUENCE: 2
atgcggctcg ttgcttccct aacggccttg gtggccttgt ccgtacctgt ctttcccgct   60
gctgtcaacg tgaagcgtgc ttcgtcctac ctggagatca ctctgagcca ggtcagcaac   120
actctgatca aggccgtggt ccagaacact ggtagcgacg agttgtcctt cgttcacctg   180
aacttcttca aggacccgc tcctgtcaaa aaggtatcgt tctatcgcga tgggtctgaa   240
gtgcagttcg agggcatttt gagccgctac aaatcgactg gcctctctcg tgacgccttt   300
acttatctgg ctcccggaga gtccgtcgag acgttttg atattgcttc gacttacgat   360
ctgaccagcg gcggccctgt aactatccgt actgaggag ttgttcccta cgccacggct   420
aacagcagcg atattgccgg ctacatctca tactcgtca atgtgttgac cattgatgtc   480
gatggcgccg ctgctgccac tgtctccaag gcaatcactc ttttggaccg ccgcactagg   540
atcagttcct gctccggcag cagacagagc gctcttacta cggctctcag aaacgctgct   600
tctcttgcca acgcagctgc cgacgcggct cagtctggat cagcttcaaa gttcagcgag   660
tacttcaaga ctacttctag ctctacccgc cagaccgtgg ctcgcgtct tcggctgtc   720
gcgcgggagg catcttcgtc ttcttcggga gccaccacgt actactgcga cgatcctac   780
ggctactgtt cctccaacgt cctggcttac accctgcctt catacaacat aatcgccaac   840
tgtgacattt tctatactta cctgccggct ctgaccagta cctgtcacgc tcaggatcaa   900
gcgccactg cccttcacga gttcacccat gcgcctggc tctacagcc tggcacggac   960
gacctggcgt atggctacca ggctgcgatg gtctcagca gcagccaggc tgtcatgaac  1020
gctgacacct acgctctcta tgcgaatgcc atataccttg gttgctaa             1068

SEQ ID NO: 3               moltype = AA   length = 355
FEATURE                    Location/Qualifiers
source                     1..355
                           mol_type = protein
                           organism = Thermoascus aurantiacus
SEQUENCE: 3
MRLVASLTAL VALSVPVFPA AVNVKRASSY LEITLSQVSN TLIKAVVQNT GSDELSFVHL    60
NFFKDPAPVK KVSVYRDGSE VQFEGILSRY KSTGLSRDAF TYLAPGESVE DVFDIASTYD   120
LTSGGPVTIR TEGVVPYATA NSTDIAGYIS YSSNVLTIDV DGAAAATVSK AITPLDRRTR   180
ISSCSGSRQS ALTTALRNAA SLANAAADAA QSGSASKFSE YFKTTSSSTR QTVAARLRAV   240
AREASSSSSG ATTYYCDDPY GYCSSNVLAY TLPSYNIIAN CDIFYTYLPA LTSTCHAQDQ   300
ATTALHEFTH APGVYSPGTD DLAYGYQAAM GLSSSQAVMN ADTYALYANA IYLGC        355

SEQ ID NO: 4               moltype = AA   length = 412
FEATURE                    Location/Qualifiers
REGION                     1..412
                           note = mat_peptide - Pyrococcus furiosus protease (Pfu)
source                     1..412
                           mol_type = protein
                           organism = Pyrococcus furiosus
SEQUENCE: 4
AELEGLDESA AQVMATYVWN LGYDGSGITI GIIDTGIDAS HPDLQGKVIG WVDFVNGRSY    60
PYDDHGHGTH VASIAAGTGA ASNGKYKGMA PGAKLAGIKV LGADGSGSIS TIIKGVEWAV   120
DNKDKYGIKV INLSLGSSQS SDGTDALSQA VNAAWDAGLV VVVAAGNSGP NKYTIGSPAA   180
ASKVITVGAV DKYDVITSFS SRGPTADGRL KPEVVAPGNW IIAARASGTS MGQPINDYYT   240
AAPGTSMATP HVAGIAALLL QAHPSWTPDK VKTALIETAD IVKKPDEIADI AYGAGRVNAY   300
KAINYDNYAK LVFTGYVANK GSQTHQFVIS GASFVTATLY WDNANSDLDL YLYDPNGNQV   360
DYSYTAYYGF EKVGYYNPTD GTWTIKVVSY SGSANYQVDV VSDGSLSQPG SS           412

SEQ ID NO: 5               moltype = DNA   length = 49
FEATURE                    Location/Qualifiers
misc_feature               1..49
                           note = Primer
source                     1..49
                           mol_type = other DNA
                           organism = synthetic construct
SEQUENCE: 5
aacgacggta cccgggggatc ggatccatgc ggctcgttgc ttccctaac                49

SEQ ID NO: 6               moltype = DNA   length = 48
FEATURE                    Location/Qualifiers
misc_feature               1..48
                           note = Primer
source                     1..48
                           mol_type = other DNA
                           organism = synthetic construct
SEQUENCE: 6
ctaattacat gatgcggccc ttaattaatt agcaaccaag gtatatgg                  48

SEQ ID NO: 7               moltype = DNA   length = 20
```

```
FEATURE                 Location/Qualifiers
misc_feature            1..20
                        note = Primer
source                  1..20
                        mol_type = other DNA
                        organism = synthetic construct
SEQUENCE: 7
taggagttta gtgaacttgc                                              20

SEQ ID NO: 8            moltype = DNA  length = 18
FEATURE                 Location/Qualifiers
misc_feature            1..18
                        note = Primer
source                  1..18
                        mol_type = other DNA
                        organism = synthetic construct
SEQUENCE: 8
ttcgagcgtc ccaaaacc                                                18

SEQ ID NO: 9            moltype = AA  length = 430
FEATURE                 Location/Qualifiers
SIGNAL                  1..22
REGION                  33..430
                        note = mat_peptide
source                  1..430
                        mol_type = protein
                        organism = Rhizomucor miehei
SEQUENCE: 9
MLFSQITSAI LLTAASLSLT TARPVSKQSE SKDKLLALPL TSVSRKFSQT KFGQQQLAEK    60
LAGLKPFSEA AADGSVDTPG YYDFDLEEYA IPVSIGTPGQ DFLLLFDTGS SDTWVPHKGC   120
TKSEGCVGSR FFDPSASSTF KATNYNLNIT YGTGGANGLY FEDSIAIGDI TVTKQILAYV   180
DNVRGPTAEQ SPNADIFLDG LFGAAYPDNT AMEAEYGSTY NTVHVNLYKQ GLISSPLFSV   240
YMNTNSGTGE VVFGGVNNTL LGGDIAYTDV MSRYGGYYFW DAPVTGITVD GSAAVRFSRP   300
QAFTIDTGTN FFIMPSSAAS KIVKAALPDA TETQQGWVVP CASYQNSKST ISIVMQKSGS   360
SSDTIEISVP VSKMLLPVDQ SNETCMFIIL PDGGNQYIVG NLFLRFFVNV YDFGNNRIGF   420
APLASAYENE                                                         430

SEQ ID NO: 10           moltype = AA  length = 368
FEATURE                 Location/Qualifiers
SIGNAL                  1..32
REGION                  33..368
                        note = mat_peptide
source                  1..368
                        mol_type = protein
                        organism = Thermobifida fusca
SEQUENCE: 10
MNHSSRRTTS LLFTAALAAT ALVAATTPAS AQELALKRDL GLSDAEVAEL RAAEAEAVEL    60
EEELRDSLGS DFGGVYLDAD TTEITVAVTD PAAVSRVDAD DVTVDVVDFG ETALNDFVAS   120
LNAIADTADP KVTGWYTDLE SDAVVITTLR GGTPAAEELA ERAGLDERAV RIVEEDEEPQ   180
SLAAIIGGNP YYFGNYRCSI GFSVRQGSQT GFATAGHCGS TGTRVSSPSG TVAGSYFPGR   240
DMGWVRITSA DTVTPLVNRY NGGTVTVTGS QEAATGSSVC RSGATTGWRC GTIQSKNQTV   300
RYAEGTVTGL TRTTACAEGG DSGGPWLTGS QAQGVTSGGT GDCRSGGITF FQPINPLLSY   360
FGLQLVTG                                                           368

SEQ ID NO: 11           moltype = AA  length = 583
FEATURE                 Location/Qualifiers
REGION                  1..583
                        note = Hybrid protein sequence
source                  1..583
                        mol_type = protein
                        organism = synthetic construct
SEQUENCE: 11
ATSDDWKGKA IYQLLTDRFG RADDSTSNCS NLSNYCGGTY EGITKHLDYI SGMGFDAIWI    60
SPIPKNSDGG YHGYWATDFY QLNSNFGDES QLKALIQAAH ERDMYVMLDV VANHAGPTSN   120
GYSGYTFGDA SLYHPKCTID YNDQTSIEQC WVADELPDID TENSDNVAIL NDIVSGWVGN   180
YSFDGIRIDT VKHIRKDFWT GYAEAAGVFA TGEVFNGDPA YVGPYQKYLP SLINYPMYYA   240
LNDVFVSKSK GFSRISEMLG SNRNAFEDTS VLTTFVDNHD NPRFLNSQSD KALFKNALTY   300
VLLGEGIPIV YYGSEQGFSG GADPANREVL WTTNYDTSSD LYQFIKTVNS VRMKSNKAVY   360
MDIYVGDNAY AFKHGDALVV LNNYGSGSTN QVSFSVSGKF DSGASLMDIV SNITTTVSSD   420
GTVTFNLKDG LPAIFTSATG GTTTTATPTG SGSVTSTSKT TATASKTSTS TSSTSCTTPT   480
AVAVTFDLTA TTTYGENIYL VGSISQLGDW ETSDGIALSA DKYTSSDPLW YVTVTLPAGE   540
SFEYKFIRIE SDDSVEWESD PNREYTVPQA CGTSTATVTD TWR                    583

SEQ ID NO: 12           moltype = AA  length = 573
FEATURE                 Location/Qualifiers
SIGNAL                  1..17
REGION                  18..573
                        note = mat_peptide
source                  1..573
```

```
                            mol_type = protein
                            organism = Gloeophyllum sepiarium
SEQUENCE: 12
MYRFLVCALG  LAASVLAQSV  DSYVSSEGPI  AKAGVLANIG  PNGSKASGAS  AGVVVASPST   60
SDPDYWYTWT  RDSSLVFKSL  IDQYTTGIDS  TSSLRTLIDD  FVTAEANLQQ  VSNPSGTLTT  120
GGLGEPKFNV  DETAFTGAWG  RPQRDGPALR  STALITYGNW  LLSNGNTSYV  TSNLWPIIQN  180
DLGYVVSYWN  QSTYDLWEEV  DSSSFFTTAV  QHRALREGAA  FATAIGQTSQ  VSSYTTQADN  240
LLCFLQSYWN  PSGGYITANT  GGGRSGKDAN  TLLASIHTYD  PSAGCDAATF  QPCSDKALSN  300
LKVYVDSFRS  VYSINSGVAS  NAAVATGRYP  EDSYQGGNPW  YLTTFAVAEQ  LYDALNVWES  360
QGSLEVTSTS  LAFFQQFSSG  VTAGTYSSSS  STYSTLTSAI  KNFADGFVAI  NAKYTPSNGG  420
LAEQYSKSDG  SPLSAVDLTW  SYASALTAFE  ARNNTQFAGW  GAAGLTVPSS  CSGNSGGPTV  480
AVTFNVNAET  VWGENIYLTG  SVDALENWSA  DNALLLSSAN  YPTWSITVNL  PASTAIEYKY  540
IRKNNGAVTW  ESDPNNSITT  PASGSTTEND  TWR                                573

SEQ ID NO: 13              moltype = AA  length = 573
FEATURE                    Location/Qualifiers
SIGNAL                     1..18
REGION                     19..573
                            note = mat_peptide
source                     1..573
                            mol_type = protein
                            organism = Pycnoporus sanguineus
SEQUENCE: 13
MRFTLLASLI  GLAVGAFAQS  SAVDAYVASE  SPIAKQGVLN  NIGPNGSKAH  GAKAGIVVAS   60
PSTENPDYLY  TWTRDSSLVF  KLLIDQFTSG  DDTSLRGLID  DFTSAEAILQ  QVSNPSGTVS  120
TGGLGEPKFN  IDETAFTGAW  GRPQRDGPAL  RATSIIRYAN  WLLDNGNTTY  VSNTLWPVIQ  180
LDLDYVADNW  NQSTFDLWEE  VDSSSFFTTA  VQHRALREGA  TFASRIGQSS  VVVSGYTTQAD 240
NLLCFLQSYW  NPSGGYVTAN  TGGGRSGKDS  NTVLTSIHTF  DPAAGCDAAT  FQPCSDKALS  300
NLKVYVDAFR  SIYTINNGIA  SNAAVATGRY  PEDSYMGGNP  WYLTTSAVAE  QLYDALYVWD  360
QLGGLNVTST  SLAFFQQFAS  GLSTGTYSAS  SSTYATLTVA  IRSFADGFLA  INAKYTPADG  420
GLAEQYSRND  GTPLSAVDLT  WSYAAALTAF  AAREGKTYGS  WGAAGLTVPA  SCSGGGGATV  480
AVTFNVQATT  VFGENIYITG  SVAALQNWSP  DNALILSSAAN YPTWSITVNL  PANTVVQYKY  540
IRKFNGQVTW  ESDPNNQITT  PSGGSFTQND  VWR                                573

SEQ ID NO: 14              moltype = AA  length = 564
FEATURE                    Location/Qualifiers
SIGNAL                     1..17
REGION                     18..564
                            note = mat_peptide
source                     1..564
                            mol_type = protein
                            organism = Meripilus giganteus
SEQUENCE: 14
MVATSLLVAS  LFTLALGTPT  GRNLKLHEAR  EDLPAGFSLR  GAASPDTTLK  LRIALVQNNF   60
AELEDKLYDV  STPSSANYGN  HLSKEEVEQY  IAPAPESVKA  VNAWLTENGL  DAHTISPAGD  120
WLAFEVPVSK  ANELFDADFS  VFTHDESGLE  AIRTLAYSIP  AELQGHLDLV  HPTVTFPNPN  180
AHLPVVRSTQ  PIRNLTGRAI  PASCASTITP  ACLQAIYGIP  TTKATQSSNK  LAVSGFIDQF  240
ANKADLKSFL  AQFRKDISSS  TTFSLQTLDG  GENDQSPSEA  GIEANLDIQY  TVGLATGVPT  300
TFISVGDDFQ  DGNLEGFLDI  INFLLGESNP  PQVLTTSYGQ  NENTISAKLA  NQLCNAYAQL  360
GARGTSILFA  SGDGGVSGSQ  SAHCSNFVPT  FPSGCPFMTS  VGATQGVSPE  TAAAFSSGGF  420
SNVFGIPSYQ  ASAVSGYLSA  LGSTNSGKFN  RSGRGFPDVS  TQGVDFQIVS  GGQTIGVDGT  480
SCASPTFASV  ISLVNDRLIA  AGKSPLGFLN  PFLYSSAGKA  ALNDVTSGSN  PGCSTNGFPA  540
KAGWDPVTGL  GTPNFAKLLT  AVGL                                           564

SEQ ID NO: 15              moltype = AA  length = 640
FEATURE                    Location/Qualifiers
SIGNAL                     1..18
REGION                     19..640
                            note = mat_peptide
source                     1..640
                            mol_type = protein
                            organism = Kionochaeata sp
SEQUENCE: 15
MRTSSILSLA  LGASVAQAAV  SPADVLAVVE  KRVDPASGLE  ARSIWDTIWD  DIKSAADCTA   60
CEAVLTLLKG  VAAFGDSFFV  EVLTEICDLS  GAEDDDVCSG  VLSLEGPILA  NDIRKMSIGS  120
KTSELFCITF  LGLCSYPDVD  AYKVPFPTAS  SAATRPVSSG  KDPLYVVHFS  DIHIDPFYVA  180
GSASNCTKPI  CCRDYTSASS  PGNNDSPAGP  YGDHNCDVPY  SLEDSMYAAI  KELVPNAAFG  240
IFTGDIVDHA  VWNTSESQNI  IDMNDAYSRM  KSSGMLPAIF  ATAGNHEASP  VNAFPPPAVG  300
KESQWVYDTL  ASDWSQWIGA  SAASSVESQG  AYSVLYGSTK  LRIISLNTNM  YYIENFYLYE  360
PTMETDPAGQ  FAWLVSELSA  AEAAGERVWI  IGHMPMGLSD  AFHNPSNYFD  QIVNRYQATI  420
AALFFGHTHE  DHFQISYSDY  GAQTAANARA  ISYIMPSLTP  TSGHPTFRVY  AVDPETFGVL  480
DATTYYADMG  LASYQTAGPT  WKPYYSARDA  YGGLVDPPLP  AGAELTPAFW  HNVTAALAAN  540
QTSFDAYYAR  KTRGWDVAPC  TGACATAEIC  ALRAARAQNN  CVVPTPGVHF  SKRATDEAEG  600
AHHRDECGIS  VARNSLSSLV  ARREALEHLE  SRLVERRRAV                         640

SEQ ID NO: 16              moltype = AA  length = 610
FEATURE                    Location/Qualifiers
SIGNAL                     1..16
REGION                     17..610
```

```
                        note = mat_peptide
source                  1..610
                        mol_type = protein
                        organism = Penicillium emersonii
SEQUENCE: 16
MRVLALIAAL ATVATASAPY DKRDLAQEIW DDIKNAVDCA GCQVVLTALK GVADLGTTAL    60
VDVLTEVCNI SGKEDSDVCS GIISREGPVL DYVLQHLDIG SHTSQVICAS AFGLCQYPEV   120
RPYNLTFPKP KPNTTRPEPS GESPIQVVHF SDTHVDLSYE TGSNYNCTKP ICCRPYTAED   180
APGNTTTPCG PYGNTKCDAP LSLEESMFAA IKALNPQPAF SIYTGDVVAH DIWLVDQNEV   240
IEDLNATYDR MAGLGLVYAA IGNHDTAPVN DLPTSNIPSE YSANWTYEAL SYDFTMLTQS   300
ASAQTAANYG SYSAIYPGSY GTDLRVISYN SIFYYVDNFW AYQDPMEFDP DGQLAWLINE   360
LQEAETAGQR VWIIAHVPTG TSDHFHDYSH YFDQIVQRYE ATIAALFYGH THIDQFQISY   420
SNYSNRAFDT ATAIGYIMPS LTPTSGPPTF RVYDVDPKTF AVLDFTNYIA NISDPAFQSG   480
PSWQKYYSAK ETYGSLLSPP VTDPTAELTP AFWHNVTVAF EQDNATFQEY WARQTRGYDV   540
SSCTGSCITQ AICGLRAGDA QYNCVTPTPG FNFAKRDTSN PKQALSHVEK CEGSGLLGLL   600
RRMVADSKSS                                                          610

SEQ ID NO: 17           moltype = AA   length = 278
FEATURE                 Location/Qualifiers
SIGNAL                  1..33
REGION                  34..278
                        note = mat_peptide
source                  1..278
                        mol_type = protein
                        organism = Bacillus thuringensis
SEQUENCE: 17
MKHHRFRTNL LSALSVSSIV ITSIIGSTQT TYAWSADAPH DPNQSTHLFI VNGAVNLVAN    60
NTDPQINKPT ALLQQWRSQW EQGLYDADHL NPYYDSGTFM SHFYDPDTQT NYAGLSYPTA   120
RQTGAKYFTI ASNDYQAGDM SDAFYNLGLS LHYFTDVTMP LHAGNISNLD HEAPGYHAKL   180
EAYAESIQNQ VTPPTAGLYN WVSPNDPELW IHQAAVQAKS VLPQVWNSDI TSWFWEAAFS   240
NYYSQQWHNA VTTPVLNQLS QAEAETAGYI DLFFRVNG                           278
```

PROCESS OF EXTRACTING OIL FROM THIN STILLAGE

CROSS-REFERENCE TO RELATED APPLICATIONS

This application is a continuation of U.S. application Ser. No. 17/306,001 filed May 3, 2021, which is a continuation of U.S. application Ser. No. 16/787,203 filed Feb. 11, 2020, now U.S. patent Ser. No. 11/028,378, which is a continuation of U.S. application Ser. No. 16/062,519 filed Jun. 14, 2018, now U.S. Pat. No. 10,597,645, which is a 35 U.S.C. 371 national application of international application no. PCT/US2016/067080 filed Dec. 16, 2016, which claims priority or the benefit under 35 U.S.C. 119 of U.S. application nos. 62/271,182, 62/271,063, 62/324,107 and 62/430,695, filed Dec. 22, 2015, Dec. 22, 2015, Apr. 18, 2016 and Dec. 6, 2016, respectively, the contents of which are fully incorporated herein by reference.

This application contains a Sequence Listing in computer readable form. The contents of the electronic sequence listing created on May 8, 2023, named SQ_ST26.xml and 30 KB in size, is hereby incorporated by reference in its entirety.

FIELD OF THE INVENTION

The present invention relates to processes of extracting/recovering oil from thin stillage and/or syrup at the backend of a fermentation product production process based on starch-containing material.

BACKGROUND OF THE INVENTION

Fermentation products, such as ethanol, are typically produced by first grinding starch-containing material in a dry-grind or wet-milling process, then degrading the material into fermentable sugars using enzymes and finally converting the sugars directly or indirectly into the desired fermentation product using a fermenting organism. Liquid fermentation products are recovered from the fermented mash (often referred to as "beer mash"), e.g., by distillation, which separate the desired fermentation product from other liquids and/or solids. The remaining fraction is referred to as "whole stillage". The whole stillage is dewatered and separated into a solid and a liquid phase, e.g., by centrifugation. The solid phase is referred to as "wet cake" (or "wet grains") and the liquid phase (supernatant) is referred to as "thin stillage". Wet cake and thin stillage contain about 35% and 7% solids, respectively. Dewatered wet cake is dried to provide "Distillers Dried Grains" (DDG) used as nutrient in animal feed. Thin stillage is typically evaporated to provide condensate and syrup or may alternatively be recycled directly to the slurry tank as "backset". Condensate may either be forwarded to a methanator before being discharged or may be recycled to the slurry tank. The syrup may be blended into DDG or added to the wet cake before drying to produce DDGS (Distillers Dried Grain with Solubles). An increasing number of ethanol plants extract oil from the thin stillage and/or syrup/evaporated centrate as a by-product for use in biodiesel production or other biorenewable products.

Much of the work in oil recovery/extraction from fermentation product production processes has focused on improving the extractability of the oil from the thin stillage. Effective removal of oil is often accomplished by hexane extraction. However, the utilization of hexane extraction has not seen widespread application due to the high capital investment required. Therefore, other processes that improve oil extraction from fermentation product production processes have been explored.

WO 2011/126897 (Novozymes) discloses processes of recovering oil by converting starch-containing materials into dextrins with alpha-amylase; saccharifying with a carbohydrate source generating enzyme to form sugars; fermenting the sugars using fermenting organism; wherein the fermentation medium comprises a hemicellulase; distilling the fermentation product to form whole stillage; separating the whole stillage into thin stillage and wet cake; and recovering oil from the thin stillage. The fermentation medium may further comprise a protease.

WO 2014/209789 (Novozymes) discloses processes of recovering oil after liquefaction and/or from thin stillage and/or syrup/evaporated centrate from a fermentation product production process by adding a thermostable protease to the whole stillage, thin stillage and/or syrup It is an object of the present invention to provide improved processes for increasing the amount of recoverable oil from fermentation product production processes.

SUMMARY OF THE INVENTION

The object of the present invention is to provide improved processes of extracting or recovering oil at the backend of a fermentation product production process, such as especially an ethanol production process.

Therefore, in the first aspect the invention relates to processes of recovering oil, comprising
    (a) converting a starch-containing material into dextrins with an alpha-amylase;
    (b) saccharifying the dextrins using a carbohydrate source generating enzyme to form a sugar;
    (c) fermenting the sugar in a fermentation medium into a fermentation product using a fermenting organism;
    (d) recovering the fermentation product to form a whole stillage;
    (e) separating the whole stillage into thin stillage and wet cake;
    (e') optionally concentrating the thin stillage into syrup;
    (f) recovering oil from the thin stillage and/or optionally the syrup, wherein a protease and a phospholipase are present and/or added during steps (a) to (c).

In an embodiment the protease and the phospholipase are present and/or added during step (b) and/or step (c). If step (a) is carried out above the initial gelatinization temperature, such as between 70-100° C., preferably between 80-90° C., such as around 85° C., a thermostable protease may also be present in and/or added in starch-containing material converting step (a).

Steps (b) and (c) may be carried out simultaneously or sequentially. In embodiments steps (a), (b) and (c) are carried our simultaneously or sequentially. When steps (a), (b) and (c), or steps (b) and (c), are carried out simultaneously, the temperature is below the initial gelatinization temperature, such as between 20-60° C., preferably between 25-40° C., such as around 32° C.

The oil may according to the invention be recovered from the thin stillage and/or syrup/evaporated centrate, e.g., by extraction, such as hexane extraction, or by using another oil recovery technology well-known in the art.

In an embodiment the protease added in steps (a)-(c) carried out at a temperature below the initial gelatinization temperature; or steps (b) and/or (c) carried out at a temperature below the initial gelatinization temperature, where step (a) is carried out at a temperature above the initial gelatinization temperature, may preferably be a protease of the peptidase family S53 protease, e.g., derived from a strain of *Meripilus*, preferably a strain of *Meripilus giganteus*, e.g., the one shown as SEQ ID NO: 14 herein; or the mature protease derived from *Thermoascus aurantiacus* shown in SEQ ID NO: 3 herein. The protease is in accordance with the invention combined with a phospholipase, e.g., derived from Kionochaeata sp. (e.g., SEQ ID NO: 15), *Penicillium emersonii* (e.g., SEQ ID NO: 16) and *Bacillus thuringiensis* (e.g., SEQ ID NO: 17), with phospholipase from *Penicillium emersonii* being preferred.

In an embodiment, the protease added in step (a) carried out above the initial gelatinization temperature may be any protease having a thermostability value, as defined herein, of more than 20% determined as Relative Activity. "Relative Activity" and "Remaining Activity" are determined as described in Example 1. In an embodiment the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. In an embodiment the protease added in step (a) carried out above the initial gelatinization temperature has a thermostability of above 90%, above 100% at 85° C. as determined using the Zein-BCA assay as disclosed in Example 2.

In an embodiment said protease added in step (a) at a temperature above the initial gelatinization temperature is a thermostable variant of the parent protease derived from *Thermoascus aurantiacus* shown in SEQ ID NO: 3 herein, classified as EC 3.4.24.39, or one having a sequence identity thereto of at least 60%, at least 70%, at least 80%, at least 90%, at least 95%, at least 96%, at least 97%, at least 98%, at least 99%, but less than 100%.

This includes the thermostable protease variants of the parent protease shown in SEQ ID NO: 3, having one of the following set of substitutions:

D79L+S87P+A112P+D142L
D79L+Y82F+S87P+A112P+D142L
S38T+D79L+S87P+A112P+A126V+D142L
D79L+Y82F+S87P+A112P+A126V+D142L
A27K+D79L+S87P+A112P+A126V+D142L
S49P+D79L+S87P+A112P+D142L
S50P+D79L+S87P+A112P+D142L
D79L+S87P+D104P+A112P+D142L
D79L+Y82F+S87G+A112P+D142L
S70V+D79L+Y82F+S87G+Y97W+A112P+D142L
D79L+Y82F+S87G+Y97W+D104P+A112P+D142L
S70V+D79L+Y82F+S87G+A112P+D142L
D79L+Y82F+S87G+D104P+A112P+D142L
D79L+Y82F+S87G+A112P+A126V+D142L
Y82F+S87G+S70V+D79L+D104P+A112P+D142L
Y82F+S87G+D79L+D104P+A112P+A126V+D142L
A27K+D79L+Y82F+S87G+D104P+A112P+A126V+D142L
A27K Y82F S87G D104P A112P A126V D142L
A27K D79L Y82F D104P A112P A126V D142L
A27K Y82F D104P A112P A126V D142L

In a preferred embodiment the thermostable protease is a variant of the parent protease (e.g., derived from *Thermoascus aurantiacus*) shown in SEQ ID NO: 3 herein with the following substitutions:

A27K+D79L+Y82F+S87G+D104P+A112P+A126V+D142L;
D79L+Y82F+S87G+A112P+D142L;
Y82F+S87G+S70V+D79L+D104P+A112P+D142L;
Y82F+S87G+D79L+D104P+A112P+A126V+D142L
(using SEQ ID NO: 3 herein for numbering).

All of these protease variants have a higher thermostability value (as defined herein) than the (wild-type) parent protease shown in SEQ ID NO: 3 herein.

In an embodiment the protease added in step (a) carried out above the initial gelatinization temperature may be a filamentous fungus, e.g., a protease classified as EC 3.4.23.23, such as derived from a strain of *Rhizomucor*, such as *Rhizomucor miehei*, such as the protease shown in SEQ ID NO: 9 herein or one having a sequence identity thereto of at least 60%, at least 70%, at least 80%, at least 90%, at least 95%, at least 96%, at least 97%, at least 98%, at least 99%.

In an embodiment the protease added in step (a) carried out above the initial gelatinization temperature is a thermostable protease derived from the bacterium, e.g., classified as EC 3.4.21.62, such as *Pyrococcus furiosus*, such as the protease shown in SEQ ID NO: 4 herein or a protease having a sequence identity thereto of at least 60%, at least 70%, at least 80%, at least 90%, at least 95%, at least 96%, at least 97%, at least 98%, at least 99%.

In an embodiment the protease added in step (a) carried out above the initial gelatinization temperature may be a bacterial serine protease, such as one derived from a strain of *Thermobifida*, such as *Thermobifida fusca*, such as the protease shown in SEQ ID NO: 10 herein or one having a sequence identity thereto of at least 60%, at least 70%, at least 80%, at least 90%, at least 95%, at least 96%, at least 97%, at least 98%, at least 99%.

In an embodiment of the invention the protease is added in a concentration of 0.01-100, such 0.1-10 micro g/g DS.

In another aspect the invention relates to the use of a protease and a phospholipase, in particular phospholipase C for oil recovery from thin stillage and/or syrup at the backend of a fermentation product production process based on starch-containing material.

BRIEF DESCRIPTION OF THE DRAWING

FIG. 1 schematically shows an ethanol production process. Oil may be recovered/extracted from the thin stillage and/or the syrup/centrate. The boxes in the FIGURE indicate where oil may be recovered/extracted.

DETAILED DESCRIPTION OF THE INVENTION

The object of the present invention is to provide improved processes of extracting or recovering oil at the backend of a fermentation product production process, such as especially an ethanol production process.

The invention relates to the use of a protease and a phospholipase in a fermentation product production process. The use of both enzymes in combination improves the extraction or recovery of oil. This may be due to the reduction in gumming or emulsification of the oil, allowing for an improved yield and/or quality of the oil.

Therefore, in the first aspect the invention relates to processes of recovering oil, comprising
 (a) converting a starch-containing material into dextrins with an alpha-amylase;
 (b) saccharifying the dextrins using a carbohydrate source generating enzyme to form a sugar;
 (c) fermenting the sugar in a fermentation medium into a fermentation product using a fermenting organism;

(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a protease and a phospholipase are present and/or added during steps (a) to (c).

In an embodiment the protease and the phospholipase are present and/or added during steps (b) and/or (c).

In an embodiment the protease and the phospholipase are added sequentially or simultaneously.

In an embodiment the protease, added during steps (a) to (c), preferably steps (b) and/or (c), is a serine protease, such as a peptidase family S53 protease. Serine proteases of the peptidase family S53 comprises two different types of peptidases: tripeptidyl aminopeptidases (exo-type) and endo-peptidases; as described in 1993, Biochem. J. 290:205-218 and in MEROPS protease database, release, 9.4 (31 Jan. 2011) (www.merops.ac.uk). The database is described in Rawlings, N. D., Barrett, A. J. and Bateman, A., 2010, "MEROPS: the peptidase database", *Nucl. Acids Res.* 38: D227-D233.

In a preferred embodiment the protease is a peptidase family S53 protease derived from a strain of *Meripilus*, preferably a strain of *Meripilus giganteus*. In an embodiment the protease is the mature sequence from *Meripilus giganteus* protease 3 (peptidase family S53 protease) concerned in Example 2 in WO 2014/037438 and/or shown as SEQ ID NO: 14 herein.

According to the invention the protease present and/or added in steps (a) to (c), preferably steps (b) and/or (c), may be a protease (e.g., derived from *Meripilus giganteus*) having the amino acid sequence set out in SEQ ID NO: 14 herein, or is a protease which has at least 60%, such as at least 70%, such as at least 80%, such as at least 85%, such as at least 90%, such as at least 95%, such as at least 96%, such as at least 97%, such as at least 98%, such as at least 99% identity SEQ ID NO: 14 herein.

In another embodiment the protease present and/or added in steps (a) to (c), preferably (b) and/or (c), may be a protease (e.g., derived from *Thermoascus aurantiacus*) having the amino acid sequence set out in SEQ ID NO: 3 herein, or is a protease which has at least 60%, such as at least 70%, such as at least 80%, such as at least 85%, such as at least 90%, such as at least 95%, such as at least 96%, such as at least 97%, such as at least 98%, such as at least 99% identity SEQ ID NO: 3 herein.

According to the invention a phospholipase is present and/or added in steps (a) to (c), preferably step (b) and/or (c) in combination with the protease. In case the temperature in step (a) is below the initial gelatinization temperature the phospholipase may be added in step (a). If the temperature in step (a) is above the initial gelatinization temperature the phospholipase is preferably added in steps (b) and/or (c).

In a preferred embodiment the phospholipase is a phospholipase C.

Examples of phospholipases, present and/or added in steps (a) to (c), preferably steps (b) and/or (c), includes those having the amino acid sequences of SEQ ID NO: 15 herein; SEQ ID NO: 16 herein; and SEQ ID NO: 17 herein.
Preferred is the phospholipase having the amino acid sequence of SEQ ID NO: 16 herein.

In an embodiment the phospholipase may be derived from *Kionochaeta*, such as the phospholipase shown in SEQ ID NO: 15 herein or one having a sequence identity thereto of at least 60%, at least 70%, at least 80%, at least 90%, at least 95%, at least 96%, at least 97%, at least 98%, at least 99%.

In a preferred embodiment the phospholipase is derived from *Penicillium*, such as the phospholipase shown in SEQ ID NO: 16 herein or one having a sequence identity thereto of at least 60%, at least 70%, at least 80%, at least 90%, at least 95%, at least 96%, at least 97%, at least 98%, at least 99%.

In an additional embodiment the phospholipase may be derived from *Bacillus*, such as the phospholipase shown in SEQ ID NO: 17 herein or one having a sequence identity thereto of at least 60%, at least 70%, at least 80%, at least 90%, at least 95%, at least 96%, at least 97%, at least 98%, at least 99%.

In an embodiment the process of recovering oil of the invention, comprises:
(a) converting a starch-containing material into dextrins with an alpha-amylase at a temperature above the initial gelatinization temperature;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a protease and a phospholipase are present and/or added during steps (b) and/or (c).

In an embodiment, a protease may be added together with the alpha-amylase in step (a) carried out at a temperature above the initial gelatinization temperature.

The protease may be any protease having a thermostability value, as defined herein, of more than 20% and the Example 1. In an embodiment the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

In one embodiment the protease is a thermostable variant of the protease derived from *Thermoascus aurantiacus* shown in SEQ ID NO: 3 herein, or one having a sequence identity thereto of at least 90%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

In one embodiment the protease is a thermostable variant of the protease derived from *Thermoascus aurantiacus* shown in SEQ ID NO: 3 herein, or one having a sequence identity thereto of at least 95%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

In one embodiment the protease is a thermostable variant of the protease derived from *Thermoascus aurantiacus* shown in SEQ ID NO: 3 herein, or one having a sequence identity thereto of at least 99%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

In an embodiment the protease is a thermostable variant of the protease derived *Thermoascus aurantiacus* shown in SEQ ID NO: 3 herein, or one having a sequence identity thereto of at least 60%, at least 70%, at least 80%, at least 90%, at least 95%, at least 96%, at least 97%, at least 98%, at least 99%.

Examples of suitable protease variants are disclosed in the Examples below. In a preferred embodiment the protease variant is selected from the group of variants comprising the following substitutions:

A27K+D79L+Y82F+S87G+D104P+A112P+A126V+D142L;
D79L+Y82F+S87G+A112P+D142L;
Y82F+S87G+S70V+D79L+D104P+A112P+D142L;
Y82F+S87G+D79L+D104P+A112P+A126V+D142L
(using SEQ ID NO: 3 herein for numbering).

All suitable protease variants have higher thermostability value (as defined herein) than the wild-type parent protease shown in SEQ ID NO: 3 herein.

In an embodiment the protease is a filamentous fungus, e.g., derived from a strain of *Rhizomucor*, such as *Rhizomucor miehei*, such as the protease shown in SEQ ID NO: 9 herein or one having a sequence identity thereto of at least 60%, at least 70%, at least 80%, at least 90%, at least 95%, at least 96%, at least 97%, at least 98%, at least 99%.

In an embodiment the protease is derived from a strain of *Rhizomucor miehei*, such as the protease shown in SEQ ID NO: 9 herein, or one having a sequence identity thereto of at least 90%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. (See Example 3).

In a preferred embodiment the protease added in step (a) carried out at a temperature above the initial gelatinization temperature is a thermostable protease derived from the bacterium *Pyrococcus furiosus*, such as the protease shown in SEQ ID NO: 4 herein, or one having sequence identity thereto of at least 60%, at least 70%, at least 80%, at least 90%, at least 95%, at least 96%, at least 97%, at least 98%, at least 99%.

The *Pyrococcus furiosus* protease shown in SEQ ID NO: 4 herein is a thermostable bacterial protease. A commercial *Pyrococcus furiosus* protease product (Pfu S) from Takara Bio Inc. (Japan) have been found to have a thermostability value of 110% (80° C./70° C.) and 103% (90° C./70° C.) at pH 4.5 determined as described in Example 1 herein.

In an embodiment the protease is a thermostable protease derived from the bacterium *Pyrococcus furiosus*, such as the protease shown in SEQ ID NO: 4 herein, or one having a sequence identity thereto of at least 90%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. (See Example 3).

In an embodiment the protease is a thermostable protease derived from the bacterium *Pyrococcus furiosus*, such as the protease shown in SEQ ID NO: 4 herein, or one having a sequence identity thereto of at least 95%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. (See Example 3).

In an embodiment the protease is a thermostable protease derived from the bacterium *Pyrococcus furiosus*, such as the protease shown in SEQ ID NO: 4 herein, or one having a sequence identity thereto of at least 99%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. (See Example 3).

In an additional embodiment the protease is a bacterial serine protease, such as derived from a strain of *Thermobifida*, such as *Thermobifida fusca*, such as the protease shown in SEQ ID NO: 10 herein or one having a sequence identity thereto of at least 60%, at least 70%, at least 80%, at least 90%, at least 95%, at least 96%, at least 97%, at least 98%, at least 99% (See Example 3).

In one embodiment the protease is derived from a strain of *Thermobifida*, such as *Thermobifida fusca*, such as the protease shown in SEQ ID NO: 10 herein, or one having a sequence identity thereto of at least 90%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. (See Example 3).

In one embodiment the protease is derived from a strain of *Thermobifida*, such as *Thermobifida fusca*, such as the protease shown in SEQ ID NO: 10 herein, or one having a sequence identity thereto of at least 95%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. (See Example 3).

In one embodiment the protease is derived from a strain of *Thermobifida*, such as *Thermobifida fusca*, such as the protease shown in SEQ ID NO: 10 herein, or one having a sequence identity thereto of at least 99%, and wherein the protease has a thermostability value of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C. (See Example 3).

When step (a) is carried out as a liquefaction step at high temperatures, i.e., above the initial gelatinization temperature, such as at temperatures between 70-100° C., preferably between 80-90° C., such as around 85° C., the alpha-amylase is preferably a bacterial alpha-amylase.

In a preferred embodiment the alpha-amylase used in step (a), when the temperature in step (a) is above the initial gelatinization temperature, is a bacterial alpha-amylase.

Especially preferred are bacterial alpha-amylases derived from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein, in particular a *Bacillus stearothermophilus* alpha-amylase truncated, preferably to be from 485-495 amino acids long, such as around 491 amino acids long.

In a preferred embodiment the bacterial alpha-amylase is selected from the group of *Bacillus stearothermophilus* alpha-amylase variants comprising a deletion of one or two amino acids at any of positions R179, G180, I181 and/or G182, preferably the double deletion disclosed in WO 96/23873—see, e.g., page 20, lines 1-10 (hereby incorporated by reference), preferably corresponding to deletion of positions I181+G182 compared to the amino acid sequence of *Bacillus stearothermophilus* alpha-amylase set forth as SEQ ID NO: 3 disclosed in WO 99/19467 or SEQ ID NO: 1 herein or the deletion of amino acids R179 and G180 using SEQ ID NO: 3 in WO 99/19467 or SEQ ID NO: 1 herein for numbering.

In an embodiment the bacterial alpha-amylase is selected from the group of *Bacillus stearothermophilus* alpha-amylase variants with the one of the following set of mutations:

I181*+G182*;
I181*+G182*+N193F;
preferably
I181*+G182*+N193F+E129V+K177L+R179E;
I181*+G182*+N193F+V59A+Q89R+E129V+K177L+R179E+H208Y+K220P+N224L+Q254S;
I181*+G182*+N193F+V59A  Q89R+E129V+K177L+R179E+Q254S+M284V; and
I181*+G182*+N193F+E129V+K177L+R179E+K220P+N224L+S242Q+Q254S (using SEQ ID NO: 1 for numbering).

The parent *Bacillus stearothermophilus* alpha-amylase may be the one shown in SEQ ID NO: 1 or may be one having sequence identity thereto of at least 60%, at least 70%, at least 80%, at least 90%, at least 95%, at least 96%, at least 97%, at least 98%, at least 99%.

The *Bacillus stearothermophilus* alpha-amylase variant may be a variant of the one shown in SEQ ID NO: 1 or may be one having sequence identity thereto of at least 60%, at least 70%, at least 80%, at least 90%, at least 95%, at least 96%, at least 97%, at least 98%, at least 99%, but less than 100%.

In an embodiment the *Bacillus stearothermophilus* alpha-amylase variant has from 1-12 mutations, such as 1, 2, 3, 4, 5, 6, 7, 8, 9, 10, 11, or 12 mutations, compared to the parent alpha-amylase, especially the parent alpha-amylase shown in SEQ ID NO: 1.

In an embodiment the pH in step (a) is from 4-7, preferably 4.5-6.

Step (a) is followed by saccharification of dextrins in step (b). However, a process of the invention may further comprise a pre-saccharification step, i.e., after step (a), but before saccharification step (b), carried out for 40-90 minutes at a temperature between 30-65° C. When step (a) is carried out at a temperature above the initial gelatinization temperature a jet-cooking step may be carried out before in step (a). Jet-cooking may be carried out at a temperature between 95-140° C. for about 1-15 minutes, preferably for about 3-10 minutes, especially around about 5 minutes.

In a preferred embodiment a process of the invention further comprises, before step (a), the steps of:
i) reducing the particle size of the starch-containing material, preferably by dry milling;
ii) forming a slurry comprising the starch-containing material and water.

In an embodiment the process of recovering oil of the invention comprises (a) converting a starch-containing material into dextrins with an alpha-amylase at a temperature below the initial gelatinization temperature;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a protease and a phospholipase are present and/or added during steps (a) to (c).

In a preferred embodiment the saccharification step (b) and fermentation step (c) are carried out simultaneously, preferably at a temperature below the initial gelatinization temperature, or sequentially.

In an embodiment steps (a), (b), and (c) are carried out simultaneously. This is typically done at a temperature below the initial gelatinization temperature, i.e. raw starch hydrolysis process (RSH). However, steps (a), (b), and (c) may also be carried out sequentially at temperatures below the initial gelatinization temperature, such as between 20-60° C., preferably between 25-40° C., such as around 32° C.

The term "initial gelatinization temperature" means the lowest temperature at which gelatinization of the starch commences. Starch heated in water begins to gelatinize between 50° C. and 75° C.; the exact temperature of gelatinization depends on the specific starch, and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material is the temperature at which birefringence is lost in 5% of the starch granules using the method described by Gorinstein. S. and Lii. C, Starch/Starke, Vol. 44 (12) pp. 461-466 (1992).

According to the invention saccharification step (b) may be carried out at a temperature from 20-75° C., preferably from 40-70° C., such as around 60° C., and at a pH between 4 and 5.

In a preferred embodiment fermentation step (c) or simultaneous saccharification and fermentation (SSF) (i.e., combined steps (b) and (c)) are carried out carried out at a temperature between 20-60° C., preferably between 25-40° C., such as around 32° C. In an embodiment fermentation step (c) or simultaneous saccharification and fermentation (SSF) (i.e., combined steps (b) and (c)) are ongoing for 6 to 120 hours, in particular 24 to 96 hours. In an embodiment the starch-containing material converting step (a), saccharification step (b) and fermentation step (c) are carried out simultaneously or sequentially.

In an embodiment the starch-containing material converting step (a) is carried out at a temperature below the initial gelatinization temperature, preferably from 20-60° C., preferably between 25-40° C., such as around 28-36° C., such as around 32° C. In an embodiment the starch-containing material is converted to dextrins and the dextrins are saccharified to a sugar by treating the starch-containing material with an alpha-amylase and carbohydrate-source generating enzyme, in particular a glucoamylase, below the initial gelatinization temperature of the starch-containing material. In an embodiment the conversion of the starch-containing material to dextrins, the saccharification of the dextrins to sugars, and the fermentation of the sugars are carried out in a single step (i.e., raw starch hydrolysis step).

When the process of the invention is carried out as a raw starch hydrolysis process (i.e., single step process or no-cook process) the glucoamylase may preferably be derived from a strain of *Trametes*, such as a strain of *Trametes cingulata*, or a strain of *Athelia*, such as a strain of *Athelia rolfsii*. Preferred alpha-amylases used in a raw starch hydrolysis process include alpha-amylases derived from a strain *Rhizomucor*, such as a strain of *Rhizomucor pusillus*, such as a *Rhizomucor pusillus* alpha-amylase with a starch-binding domain (SBD), such as a *Rhizomucor pusillus* alpha-amylase with *Aspergillus niger* glucoamylase linker and SBD. Generally the starch-containing material in raw starch hydrolysis processes (i.e., no-cook processes) are granular starch. Said granular starch may be reduced the particle size, preferably by milling, to from 0.05 to 3.0 mm, preferably 0.1-0.5 mm.

Also the sugar level, such as glucose level, may be kept below 6 wt.-%, preferably below about 3 wt.-%, preferably below about 2 wt.-%, more preferred below about 1 wt.-%, even more preferred below about 0.5%, or even more preferred 0.25% wt.-%, such as below about 0.1 wt.-%. The pH may be from 4-7, preferably 4.5-6.0, when conversion of the starch-containing material to dextrins, the saccharification of the dextrins to a sugar, and the fermentation of the sugar are carried out in a single step. If the process of the invention is carried out as a conventional process (i.e., step (a) is carried out as a liquefaction step at a temperature above the gelatinization temperature) the carbohydrate-source generating enzyme used in step (b) is preferably a glucoamylase derived from *Aspergillus*, preferably *A. niger*, *A. awamori*, or *A. oryzae*; or a strain of *Trichoderma*, preferably *Trichoderma reesei*; or a strain of *Talaromyces*, preferably *Talaromyces emersonii*, or a strain of Pycnoporus, or a strain of Gloephyllum.

Examples of other suitable glucoamylase can be found below in the "Glucoamylases" section below.

Generally the starch-containing material in step (a), including granular starch, contains 20-55 wt.-% dry solids, preferably 25-40 wt.-% dry solids, more preferably 30-35% dry solids.

Separation (i.e. dewatering) in step (e) may be carried out by centrifugation, preferably a decanter centrifuge, filtration, preferably using a filter press, a screw press, a plate-and-frame press, a gravity thickener or decker or any other separation technology known in the art.

The (desired) fermentation product may in an embodiment be selected from the group consisting of alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, B12, beta-carotene); and hormones. In a preferred embodiment the (desired) fermentation product is ethanol. According to the invention the desired fermentation product may be recovered by distillation. According to the invention oil may be recovered from the thin stillage and/or syrup/evaporated centrate, e.g., by extraction, such as hexane extraction.

Separating (Dewatering) Whole Stillage into Thin Stillage and Wet Cake in Step (e)

Separating whole stillage into thin stillage and wet cake in step (e), in order to remove a significant portion of the liquid/water, may be done using any suitable separation technique, including centrifugation, pressing and filtration. In a preferred embodiment the separation/dewatering is carried out by centrifugation. Preferred centrifuges in industry are decanter type centrifuges, preferably high speed decanter type centrifuges. An example of a suitable centrifuge is the NX 400 steep cone series from Alfa Laval which is a high-performance decanter. In another preferred embodiment the separation is carried out using other conventional separation equipment such as a plate/frame filter presses, belt filter presses, screw presses, gravity thickeners and deckers, or similar equipment.

Drying of Wet Cake

After the wet cake, containing about 30-35 wt-% dry solids, has been separated from the thin stillage (e.g., dewatered) it may be dried in a drum dryer, spray dryer, ring drier, fluid bed drier or the like in order to produce "Distillers Dried Grains" (DDG). DDG is a valuable feed ingredient for livestock, poultry and fish. It is preferred to provide DDG with a content of less than about 10-12 wt.-% moisture to avoid mold and microbial breakdown and increase the shelf life. Further, high moisture content also makes it more expensive to transport DDG. The wet cake is preferably dried under conditions that do not denature proteins in the wet cake. The wet cake may be blended with syrup separated from the thin stillage and dried into DDG with Solubles (DDGS).

Fermenting Organisms

Examples of fermenting organisms used in step c) for fermenting sugars in a fermentation medium into a desired fermentation product include fungal organisms, such as especially yeast. Preferred yeast includes strains of *Saccharomyces* spp., in particular, *Saccharomyces cerevisiae*.

In one embodiment the fermenting organism is added to the fermentation medium, so that the viable fermenting organism, such as yeast, count per mL of fermentation medium is in the range from 105 to $10^{12}$, preferably from $10^7$ to $10^{10}$, especially about $5 \times 10^7$.

Commercially available yeast includes, e.g., RED STAR™ and ETHANOL RED yeast (available from Fermentis/Lesaffre, USA), FALI (available from Fleischmann's Yeast, USA), SUPERSTART and THERMOSACC™ fresh yeast (available from Ethanol Technology, WI, USA), BIO-FERM AFT and XR (available from NABC—North American Bioproducts Corporation, GA, USA), GERT STRAND (available from Gert Strand AB, Sweden), and FERMIOL (available from DSM Specialties).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived there from, or cereals. Contemplated are also waxy and non-waxy types of corn and barley.

Fermentation Products

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, B12, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes. The fermentation product, such as ethanol, obtained according to the invention, may be used as fuel which may be blended with gasoline. However, in the case of ethanol it may also be used as potable ethanol.

Recovery

Subsequent to fermentation the fermentation product, such as ethanol, may be separated from the fermentation medium, e.g., by distillation. Alternatively the desired fermentation product may be extracted from the fermentation medium by micro or membrane filtration techniques. The fermentation product may also be recovered by stripping or other method well known in the art.

Use of Protease and Phospholipase for Improving Oil Extraction

In an aspect, the invention relates to the use of a protease in combination with a phospholipase for increasing oil recovery yields from thin stillage and/or syrup in a fermentation product production process. FIG. 1 shows a typical fermentation product production process including where oil extraction typically is done.

Enzymes

One or more of the following enzyme activities may be used according to the invention.

Alpha-Amylases

The process of the invention, including step (a), may be carried out using a suitable alpha-amylase. In a preferably embodiment a bacterial alpha-amylase and/or a fungal alpha-amylase may be used.

The alpha-amylase may be bacterial when step (a) is carried out as a liquefaction step at high temperatures, i.e., above the initial gelatinization temperature.

The alpha-amylase may be fungal when step (a) is carried out at a temperature below the initial gelatinization temperature, such as when steps (a), (b) and (c) are carried out as a raw starch hydrolysis (single step process or no-cook process) as described above.

Bacterial Alpha-Amylases

Examples of suitable bacterial alpha-amylases include the below mentioned. Preferred bacterial alpha-amylases used in step i) may be derived from a strain the genus *Bacillus* (sometimes referred to as *Geobacillus*), including a strain of *Bacillus licheniformis, Bacillus amyloliquefaciens, Bacillus stearothermophilus*, or *Bacillus subtilis*. Other bacterial alpha-amylases include alpha-amylase derived from a strain of the *Bacillus* sp. NCIB 12289, NCIB 12512, NCIB 12513 or DSM 9375, all of which are described in detail in WO 95/26397, and the alpha-amylase described by Tsukamoto et al., Biochemical and Biophysical Research Communications, 151 (1988), pp. 25-31 (hereby incorporated by reference).

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents hereby incorporated by reference). Specifically contemplated alpha-amylase variants are disclosed in U.S. Pat. No. 6,093,562, 6,297,038 or 6,187,576 (hereby incorporated by reference) and include *Bacillus stearothermophilus* alpha-amylase (BSG alpha-amylase) variants having a deletion of one or two amino acid in positions R179 to G182, preferably a double deletion disclosed in WO 1996/023873—see e.g., page 20, lines 1-10 (hereby incorporated by reference), preferably corresponding to delta(181-182) compared to the wild-type BSG alpha-amylase amino acid sequence set forth in SEQ ID NO:3 disclosed in WO 99/19467 or SEQ ID NO: 1 herein, or deletion of amino acids R179+G180 using SEQ ID NO:3 in WO 99/19467 or SEQ ID NO: 1 herein for numbering (which reference is hereby incorporated by reference). Even more preferred are *Bacillus* alpha-amylases, especially *Bacillus stearothermophilus* alpha-amylase, which have a double deletion corresponding to delta(181-182) and optionally further comprising a N193F substitution (also denoted I181*+G182*+N193F) compared to the wild-type BSG alpha-amylase amino acid sequence set forth in SEQ ID NO:3 disclosed in WO 99/19467 or SEQ ID NO: 1 herein.

In an embodiment the *Bacillus stearothermophilus* alpha-amylase is one disclosed in WO 2011/082425, such as one selected from the group of:

I181*+G182*;
I181*+G182*+N193F;
preferably
I181*+G182*+N193F+E129V+K177L+R179E;
I181*+G182*+N193F+V59A+Q89R+E129V+K177L+ R179E+H208Y+K220P+N224L+Q254S;
I181*+G182*+N193F+V59A+Q89R+E129V+K177L+ R179E+Q254S+M284V; and
I181*+G182*+N193F+E129V+K177L+R179E+K220P+ N224L+S242Q+Q254S (using SEQ ID NO: 1 herein for numbering).

In an embodiment the *Bacillus stearothermophilus* alpha-amylase has the following mutations: 181*+G182*+ N193F+V59A+Q89R+E129V+K177L+R179E+Q254S+ M284V (SEQ ID NO: 1).

The truncated *Bacillus stearothermophilus* alpha-amylase is typically naturally truncated to be about 491 amino acids long, such as from 485-495 amino acids long.

A hybrid alpha-amylase specifically contemplated comprises 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with the following substitution: G48A+T491+G107A+H156Y+ A181T+N190F+1201F+A209V+Q264S (using the numbering in SEQ ID NO: 4 in WO 99/19467). Especially preferred are variants having one or more of the mutations H154Y, A181T, N190F, A209V and Q264S and/or deletion of two residues between positions 176 and 179, preferably deletion of E178 and G179 (using the SEQ ID NO: 5 numbering of WO 99/19467).

Commercially available bacterial alpha-amylase products and products containing alpha-amylases include TERMAMYL™ SC, LIQUOZYME™ SC, LIQUOZYME™ LpH, AVANTEC™, AVANTEC™ AMP, BAN (Novozymes A/S, Denmark) DEX-LO™, SPEZYME™ XTRA, SPEZYME™ AA, SPEZYME FRED-L, SPEZYME™ ALPHA, GC358, SPEZYME RSL, SPEZYME HPA and SPEZYME™ DELTA AA (from DuPont, USA), FUELZYME™ (Verenium, USA).

A bacterial alpha-amylase may be added in step (a) in amounts as are well-known in the art. When measured in KNU units (described below in the "Materials & Methods"-section) the alpha-amylase activity is preferably present in an amount of 0.5-5,000 NU/g of DS, in an amount of 1-500 NU/g of DS, or more preferably in an amount of 5-1,000 NU/g of DS, such as 10-100 NU/g DS.

Fungal Alpha-Amylases

Fungal alpha-amylases (EC 3.2.1.1) are preferably of filamentous fungus origin. The fungal alpha-amylase may be a fungal acid alpha-amylase.

Fungal acid alpha-amylases include acid alpha-amylases derived from a strain of the genus *Aspergillus*, such as *Aspergillus oryzae* and *Aspergillus niger* alpha-amylases.

A preferred fungal alpha-amylase is a Fungamyl-like alpha-amylase which is preferably derived from a strain of *Aspergillus oryzae*. In the present disclosure, the term "Fungamyl-like alpha-amylase" indicates an alpha-amylase which exhibits a high identity, i.e. more than 70%, more than 75%, more than 80%, more than 85% more than 90%, more than 95%, more than 96%, more than 97%, more than 98%, more than 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *A. niger* disclosed as "AMYA_ASPNG" in the Swiss-prot/TeEMBL database under the primary accession no. P56271 and described in more detail in WO 89/01969 (Example 3). The acid *Aspergillus niger* acid alpha-amylase is also shown as SEQ ID NO: 1 in WO 2004/080923 (Novozymes) which is hereby incorporated by reference. Also variants of said acid fungal amylase having at least 70% identity, such as at least 80% or even at least 90% identity, such as at least 95%, at least 96%, at least 97%, at least 98%, or at least 99% identity to SEQ ID NO: 1 in WO 2004/080923 are contemplated. A suitable commercially available acid fungal alpha-amylase derived from *Aspergillus niger* is SP288 (available from Novozymes A/S, Denmark).

The fungal acid alpha-amylase may also be a wild-type enzyme comprising a carbohydrate-binding module (CBM) and an alpha-amylase catalytic domain (i.e., a none-hybrid), or a variant thereof. In an embodiment the wild-type acid fungal alpha-amylase is derived from a strain of *Aspergillus kawachii*.

Commercial available compositions comprising fungal alpha-amylase include FUNGAMYL™ and the acid fungal alpha-amylase sold under the trade name SP288 (available from Novozymes A/S, Denmark).

In an embodiment the fungal acid alpha-amylase is a hybrid alpha-amylase. Preferred examples of fungal hybrid alpha-amylases include the ones disclosed in WO 2005/003311 or U.S. Patent Publication no. 2005/0054071 (Novozymes) or U.S. patent application No. 60/638,614 (Novozymes) which is hereby incorporated by reference. A hybrid alpha-amylase may comprise an alpha-amylase catalytic domain (CD) and a carbohydrate-binding domain/module (CBM), such as a starch binding domain, and optional a linker.

Specific examples of contemplated hybrid alpha-amylases include those disclosed in Table 1 to 5 of the examples in U.S. patent application No. 60/638,614, including Fungamyl variant with catalytic domain JA1 18 and *Athelia rolfsii* SBD and SEQ ID NO: 100 in U.S. 60/638,614), *Rhizomucor pusillus* alpha-amylase with *Athelia rolfsii* AMG linker and SBD (SEQ ID NO:101 in U.S. 60/638,614), *Rhizomucor pusillus* alpha-amylase with *Aspergillus niger* glucoamylase linker and SBD (which is disclosed in Table 5 as a combination of amino acid sequences SEQ ID NO:20, SEQ ID NO:72 and SEQ ID NO:96 in U.S. application Ser. No. 11/316,535), and *Meripilus giganteus* alpha-amylase with *Athelia rolfsii* glucoamylase linker and SBD (SEQ ID NO:102 in U.S. 60/638,614). Other specifically contemplated hybrid alpha-amylases are any of the ones listed in Tables 3, 4, 5, and 6 in Example 4 in U.S. application Ser. No. 11/316,535 or WO 2006/069290 (hereby incorporated by reference). Other specific examples of contemplated hybrid alpha-amylases include those disclosed in U.S. Patent Publication no. 2005/0054071, including those disclosed in Table 3 on page 15, such as *Aspergillus niger* alpha-amylase with *Aspergillus kawachii* linker and starch binding domain.

In a preferred embodiment the alpha-amylase is one disclosed in WO 2013/006756 including the following variants: *Rhizomucor pusillus* alpha-amylase variant having an *Aspergillus niger* glucoamylase linker and starch-binding domain (SBD) which further comprises at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 2 in WO 2013/006756 for numbering) (all incorporated by reference).

An acid alpha-amylases may according to the invention be added in an amount of 0.1 to AFAU/g DS, preferably 0.10 to 5 AFAU/g DS, especially 0.3 to 2 AFAU/g DS.

Fungal alpha-amylases may be added to step (a) in a well know effective amount, preferably in the range from 0.001-1 mg enzyme protein per g DS, preferably 0.01-0.5 mg enzyme protein per g DS.

Carbohydrate-Source Generating Enzyme

According to the invention a carbohydrate-source generating enzyme, preferably a glucoamylase, is present in step (b), and may be present and/or added during step (a), saccharification step (b) and/or fermentation step (c) or simultaneous saccharification step (b) and fermentation step (c) (SSF).

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used.

Specific examples include glucoamylase (being glucose generators), beta-amylase and maltogenic amylase (being maltose generators).

In a preferred embodiment the carbohydrate-source generating enzyme is a glucoamylase.

Glucoamylases

The process of the invention, including steps (b) and/or (c), may be carried out using any suitable glucoamylase. In a preferably embodiment the glucoamylase is of bacterial or fungal origin.

Contemplated glucoamylases include those from the group consisting of *Aspergillus* glucoamylases, in particular *A. niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *A. oryzae* glucoamylase (AgriC. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1 199-1204.

Other glucoamylases contemplated include glucoamylase derived from a strain of *Athelia*, preferably a strain of *Athelia rolfsii* (previously denoted Corticium *rolfsii*) glucoamylase (see U.S. Pat. No. 4,727,026 and (Nagasaka, Y. et al. (1998) "Purification and properties of the raw-starch-degrading glucoamylases from Corticium *rolfsii*, Appl Microbiol Biotechnol 50:323-330), *Talaromyces* glucoamylases, in particular derived from *Talaromyces emersonii* (WO 99/28448), *Talaromyces leycettanus* (U.S. Pat. No. Re. 32,153), *Talaromyces duponti, Talaromyces thermophilus* (U.S. Pat. No. 4,587,215). Also contemplated are the *Trichoderma reesei* glucoamylases disclosed as SEQ ID NO: 4 in WO 2006/060062 and glucoamylases being at least 80% or at least 90% identical thereto and further the glucoamylase derived from *Humicola grisea* disclosed as SEQ ID NO: 3 in U.S. Ser. No. 10/992,187 (hereby incorporated by reference) or sequences having at least 80% or at least 90% identity thereto.

In a preferred embodiment the glucoamylase is derived from a strain of *Aspergillus*, preferably *A. niger, A. awamori*, or *A. oryzae*; or a strain of *Trichoderma*, preferably *T reesei*; or a strain of *Talaromyces*, preferably *T emersonii*.

In an embodiment the glucoamylase present and/or added during saccharification step (b) and/or fermentation step (c) is of fungal origin, preferably from a strain of Pycnoporus, or a strain of Gloephyllum. In an embodiment the glucoamylase is derived from a strain of the genus Pycnoporus, in particular a strain of Pycnoporus *sanguineus* described in WO 2011/066576 (SEQ ID NOs 2, 4 or 6), such as the one shown as SEQ ID NO: 4 in WO 2011/066576 or SEQ ID NO: 13 herein.

In an embodiment the glucoamylase is derived from a strain of the genus Gloeophyllum, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803 or SEQ ID NO: 12 herein.

Other contemplated glucoamylases include glucoamylase derived from a strain of *Trametes*, preferably a strain of *Trametes cingulata* disclosed in WO 2006/069289 (which is hereby incorporated by reference). Also hybrid glucoamylase are contemplated according to the invention. Examples the hybrid glucoamylases disclosed in WO 2005/045018. Specific examples include the hybrid glucoamylase disclosed in Table 1 and 4 of Example 1 (which hybrids are hereby incorporated by reference).

Bacterial glucoamylases contemplated include glucoamylases from the genus *Clostridium*, in particular *C. thermoamylolyticum* (EP 135,138), and *C. thermohydrosulfuricum* (WO 86/01831).

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ ULTRA, SPIRIZYME™ EXCEL, SPIRIZYME™ ACHIEVE, SPIRIZYME™ B4U and AMG™ E (from Novozymes A/S); OPTIDEX™ 300 (from Genencor Int.); AMIGASE™ and AMIGASE™ PLUS (from DSM); G-ZYME™ G900, G-ZYME™ and G990 ZR (from Genencor Int.).

Glucoamylases may in an embodiment be added in an amount of 0.02-20 AGU/g DS, preferably 0.05-5 AGU/g DS (in whole stillage), especially between 0.1-2 AGU/g DS. Glucoamylase may be added in an effective amount, preferably in the range from 0.001-1 mg enzyme protein per g DS, preferably 0.01-0.5 mg enzyme protein per g dry solid (DS).

Phospholipases

Phospholipases act to hydrolyse phospholipids into their constituent fatty acids and lipophilic moieties. A preferred type of phospholipase is phospholipase C. Suitable phospholipases for use in the invention are derived from organisms, preferably from bacteria or fungi. Preferred phospholipases are derived from Kionochaeata sp. (e.g., SEQ ID NO: 15), *Penicillium emersonii* (e.g., SEQ ID NO: 16) and *Bacillus* thuringensis (e.g., SEQ ID NO: 17), with phospholipase from *Penicillium emersonii* being preferred.

The invention is further summarized in the following paragraphs:

1. A process of recovering oil, comprising
   (a) converting a starch-containing material into dextrins with an alpha-amylase;
   (b) saccharifying the dextrins using a carbohydrate source generating enzyme to form a sugar;
   (c) fermenting the sugar in a fermentation medium into a fermentation product using a fermenting organism;
   (d) recovering the fermentation product to form a whole stillage;
   (e) separating the whole stillage into thin stillage and wet cake;
   (e') optionally concentrating the thin stillage into syrup;
   (f) recovering oil from the thin stillage and/or optionally the syrup, wherein a protease and a phospholipase are present and/or added during steps (a) to (c).

2. The process of paragraph 1, preferably wherein the protease and the phospholipase are present and/or added during steps (b) and/or (c).

3. The process of paragraph 1 or 2, wherein the protease present and/or added in steps (a) to (c), preferably steps (b) and/or (c), is a protease (e.g., derived from *Meripilus giganteus*) having the amino acid sequence set out in SEQ ID NO: 14 herein, or is a protease which has at least 60%, such as at least 70%, such as at least 80%, such as at least 85%, such as at least 90%, such as at least 95%, such as at least 96%, such as at least 97%, such as at least 98%, such as at least 99% identity SEQ ID NO: 14 herein.

4. The process of paragraph 1 or 2, wherein the protease present and/or added in steps (a) to (c), preferably (b) and/or (c), is a protease (e.g., derived from *Thermoascus aurantiacus*) having the amino acid sequence set out in SEQ ID NO: 3 herein, or is a protease which has at least 60%, such as at least 70%, such as at least 80%, such as at least 85%, such as at least 90%, such as at least 95%, such as at least 96%, such as at least 97%, such as at least 98%, such as at least 99% identity SEQ ID NO: 3 herein.

5. The process of any of paragraphs 1-4 wherein the phospholipase, present and/or added in steps (a) to (c), preferably steps (b) and/or (c), is a phospholipase C.

6. The process of any of paragraphs 1-5, wherein the phospholipase, present and/or added in steps (a) to (c), preferably steps (b) and/or (c), has the amino acid sequence of SEQ ID NO: 15 herein; SEQ ID NO: 16 herein; or SEQ ID NO: 17 herein, preferably where the phospholipase has the amino acid sequence of SEQ ID NO: 16 herein.

7. The process of any of paragraphs 1-5, wherein the phospholipase, present and/or added in steps (a) to (c), preferably steps (b) and/or (c), is derived from *Kionochaeta*, such as the phospholipase shown in SEQ ID NO: 15 herein or one having a sequence identity thereto of at least 60%, at least 70%, at least 80%, at least 90%, at least 95%, at least 96%, at least 97%, at least 98%, at least 99%.

8. The process of any of paragraphs 1-5, wherein the phospholipase, present and/or added in steps (a) to (c), preferably steps (b) and/or (c), is derived from *Penicillium*, such as the phospholipase shown in SEQ ID NO: 16 herein or one having a sequence identity thereto of at least 60%, at least 70%, at least 80%, at least 90%, at least 95%, at least 96%, at least 97%, at least 98%, at least 99%.

9. The process of any of paragraphs 1-5, wherein the phospholipase, present and/or added in steps (a) to (c), preferably steps (b) and/or (c), is derived from *Bacillus*, such as the phospholipase shown in SEQ ID NO: 17 herein or one having a sequence identity thereto of at least 60%, at least 70%, at least 80%, at least 90%, at least 95%, at least 96%, at least 97%, at least 98%, at least 99%.

10. The process of any of paragraphs 1-9, wherein the protease and the phospholipase are added sequentially or simultaneously.

11. The process of recovering oil of any of paragraphs 1-10, comprising
(a) converting a starch-containing material into dextrins with an alpha-amylase at a temperature above the initial gelatinization temperature;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a protease and a phospholipase are present and/or added during steps (b) and/or (c).

12. The process of paragraphs 1-11, wherein the temperature in step (a) is above the initial gelatinization temperature, such as at a temperature between 80-90° C., such as around 85° C.

13. The process of any of paragraphs 11-12, wherein a protease derived from a strain of *Pyrococcus*, preferably a strain of *Pyrococcus furiosus*, is added in step (a) carried out above the initial gelatinization temperature.

14. The process of paragraphs 11-13, wherein the protease is the one shown SEQ ID NO: 4 herein, or wherein the protease has at least 60%, such as at least 70%, such as at least 80%, such as at least 85%, such as at least 90%, such as at least 95%, such as at least 96%, such as at least 97%, such as at least 98%, such as at least 99% identity SEQ ID NO: 4 herein.

15. The process of any of paragraphs 11-14, wherein the protease, added in step (a) carried out at a temperature above the initial gelatinization temperature, has a thermostability of more than 20%, more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

16. The process of any of paragraphs 11-15, wherein the protease, added in step (a) carried out at a temperature above the initial gelatinization temperature, has a thermostability between 50 and 115%, such as between 50 and 70%, such as between 50 and 60%, such as between 100 and 120%, such as between 105 and 115% determined as Relative Activity at 80° C./70° C.

17. The process of any of paragraphs 11-16, wherein the protease, added in step (a) carried out at a temperature above the initial gelatinization temperature, has a thermostability of more than 12%, more than 14%, more than 16%, more than 18%, more than 20%, more than 25%, more than 30%, more than 40%, more that 50%, more than 60%, more than 70%, more than 80%, more than 90%, more than 100%, more than 110% determined as Relative Activity at 85° C./70° C.

18. The process of any of paragraphs 11-17, wherein the bacterial alpha-amylase is derived from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein, in particular the *Bacillus* 15 *stearothermophilus* alpha-amylase is truncated, preferably to have from 485-495 amino acids, such as around 491 amino acids.

19. The process of recovering oil of paragraphs 1-10, comprising
(a) converting a starch-containing material into dextrins with an alpha-amylase at a temperature below the initial gelatinization temperature;
(b) saccharifying the dextrins using a carbohydrate source generating enzyme to form a sugar;
(c) fermenting the sugar in a fermentation medium into a fermentation product using a fermenting organism;
(d) recovering the fermentation product to form a whole stillage;
(e) separating the whole stillage into thin stillage and wet cake;
(e') optionally concentrating the thin stillage into syrup;
(f) recovering oil from the thin stillage and/or optionally the syrup, wherein a protease and a phospholipase are present and/or added during steps (a) to (c).

20. The process of paragraph 19, wherein saccharification step (b) and fermentation step (c) are carried out simultaneously, preferably at a temperature below the initial gelatinization temperature, or sequentially.

21. The process of paragraph 19, wherein steps (a), (b) and (c) are carried out simultaneously or sequentially at a temperature below the initial gelatinization temperature.
22. Use of a protease and a phospholipase for increasing oil recovery yields from thin stillage and/or syrup in a fermentation product production process.
23. The use of paragraph 22, wherein the protease (e.g., derived from *Meripilus giganteus*) has the amino acid sequence set out in SEQ ID NO: 14 herein, or is a protease which has at least 60%, such as at least 70%, such as at least 80%, such as at least 85%, such as at least 90%, such as at least 95%, such as at least 96%, such as at least 97%, such as at least 98%, such as at least 99% identity SEQ ID NO: 14 herein.
24. The use of paragraph 22, wherein the protease (e.g., derived from *Thermoascus aurantiacus*) having the amino acid sequence set out in SEQ ID NO: 3 herein, or is a protease which has at least 60%, such as at least 70%, such as at least 80%, such as at least 85%, such as at least 90%, such as at least 95%, such as at least 96%, such as at least 97%, such as at least 98%, such as at least 99% identity SEQ ID NO: 3 herein.
25. The use of any of paragraphs 22-24, wherein the phospholipase is a phospholipase C.
26. The use of any of paragraphs 22-25, wherein the phospholipase has the amino acid sequence of SEQ ID NO: 15 herein; SEQ ID NO: 16 herein; or SEQ ID NO: 17 herein, preferably where the phospholipase has the amino acid sequence of SEQ ID NO: 16 herein.
27. The use of any of paragraphs 22-26, wherein the phospholipase is derived from *Kionochaeta*, such as the phospholipase shown in SEQ ID NO: 15 herein or one having a sequence identity thereto of at least 60%, at least 70%, at least 80%, at least 90%, at least 95%, at least 96%, at least 97%, at least 98%, at least 99%.
28. The use of any of paragraphs 22-26, wherein the phospholipase is derived from *Penicillium*, such as the phospholipase shown in SEQ ID NO: 16 herein or one having a sequence identity thereto of at least 60%, at least 70%, at least 80%, at least 90%, at least 95%, at least 96%, at least 97%, at least 98%, at least 99%.
29. The use of any of paragraphs 22-26, wherein the phospholipase is derived from *Bacillus*, such as the phospholipase shown in SEQ ID NO: 17 herein or one having a sequence identity thereto of at least 60%, at least 70%, at least 80%, at least 90%, at least 95%, at least 96%, at least 97%, at least 98%, at least 99%.
30. The use of any of paragraphs 22-29, wherein the protease and the phospholipase are added sequentially or simultaneously.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties. The present invention is further described by the following examples which should not be construed as limiting the scope of the invention.

Material & Methods
  Enzymes: Alpha-Amylase LSCDS ("LSCDS"): *Bacillus stearothermophilus* alpha-amylase with the mutations: I181*+G182*+N193F truncated to be around 491 amino acids long (SEQ ID NO: 1 herein).
  Alpha-Amylase 369: (AA369): *Bacillus stearothermophilus* alpha-amylase with the mutations: I181*+G182*+N193F+V59A+Q89R+E129V+K177L+R179E+Q254S+M284V truncated to be around 491 amino acids long (SEQ ID NO: 1 herein).
  Protease OX ("OX"): Metallo protease derived from *Thermoascus aurantiacus* CGMCC No. 0670 disclosed as amino acids 1-177 in SEQ ID NO: 3 herein
  Protease PF ("PF"): Protease derived from the bacterium *Pyrococcus furiosus* shown in SEQ ID NO: 4 herein.
  Protease RH ("RH"): Protease derived from a filamentous fungus *Rhizomucor miehei* shown in SEQ ID NO: 9 herein.
  Protease TF ("TF"): Protease derived from a filamentous fungus *Thermobifida fusca* shown in SEQ ID NO: 10 herein.

Determination of Alpha-Amylase Activity
1. Phadebas™ Assay

Alpha-amylase activity is determined by a method employing Phadebas® tablets as substrate. Phadebas tablets (Phadebas® Amylase Test, supplied by Pharmacia Diagnostic) contain a cross-linked insoluble blue-colored starch polymer, which has been mixed with bovine serum albumin and a buffer substance and tableted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units. In this absorbance range there is linearity between activity and absorbance (Lambert-Beer law). The dilution of the enzyme must therefore be adjusted to fit this criterion. Under a specified set of conditions (temperature, pH, reaction time, buffer conditions) 1 mg of a given alpha-amylase will hydrolyze a certain amount of substrate and a blue colour will be produced. The measured absorbance is directly proportional to the specific activity (activity/mg of pure alpha-amylase protein) of the alpha-amylase in question under the given set of conditions.

2. Alternative Method

Alpha-amylase activity is alternatively determined by a method employing the PNP-G7 substrate. PNP-G7 which is an abbreviation for p-nitrophenyl-alpha,D-maltoheptaoside, which is a blocked oligosaccharide that can be cleaved by an endo-amylase. Following the cleavage, the alpha-glucosidase included in the kit digest the substrate to liberate a free PNP molecule which has a yellow colour and thus can be measured by visible spectophometry at wavelength Lambda=405 nm (400-420 nm). Kits containing PNP-G7 substrate and alpha-glucosidase are manufactured by Bohringer-Mannheim (cat. No. 1054635).

To prepare the substrate one bottle of substrate (BM 1442309) is added to 5 ml buffer (BM1442309). To prepare the alpha-glucosidase one bottle of alpha-glucosidase (BM 1462309) is added to 45 ml buffer (BM1442309). The working solution is made by mixing 5 ml alpha-glucosidase solution with 0.5 ml substrate.

The assay is performed by transforming 20 microL enzyme solution to a 96 well microtitre plate and incubating at 25° C. 200 microL working solution, 25° C. is added. The solution is mixed and pre-incubated 1 minute and absorption is measured every 15 seconds over 3 minutes at OD 405 nm.

The slope of the time dependent absorption-curve is directly proportional to the specific activity (activity per mg enzyme) of the alpha-amylase in question under the given set of conditions.

Determination of Acid Amylolytic Activity (FAU)

One Fungal Alpha-Amylase Unit (1 FAU) is defined as the amount of enzyme, which breaks down 5.26 g starch (Merck Amylum solubile Erg. B.6, Batch 9947275) per hour at Novozymes' standard method for determination of alpha-amylase based upon the following standard conditions:

| Substrate | Soluble starch |
|---|---|
| Temperature | 37° C. |
| pH | 4.7 |
| Reaction time | 7-20 minutes |

A detailed description of Novozymes' method for determining KNU and FAU is available on request as standard method EB-SM-0009.02/01.

Determination of acid alpha-amylase activity (AFAU)

Acid alpha-amylase activity is measured in AFAU (Acid Fungal Alpha-amylase Units), which are determined relative to an enzyme standard.

The standard used is AMG 300 L (wild type *A. niger* G1 AMG sold by Novozymes A/S). The neutral alpha-amylase in this AMG falls after storage at room temperature for 3 weeks from approx. 1 FAU/mL to below 0.05 FAU/mL.

The acid alpha-amylase activity in this AMG standard is determined in accordance with AF 9 1/3 (Novo method for the determination of fungal alpha-amylase). In this method, 1 AFAU is defined as the amount of enzyme, which degrades 5.260 mg starch dry matter per hour under standard conditions.

Iodine forms a blue complex with starch but not with its degradation products. The intensity of colour is therefore directly proportional to the concentration of starch. Amylase activity is determined using reverse colorimetry as a reduction in the concentration of starch under specified analytic conditions.

Alpha-Amylase

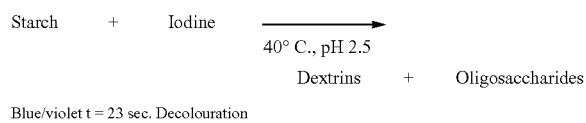

Blue/violet t = 23 sec. Decolouration

Standard Conditions/Reaction Conditions: (Per Minute)

| Substrate: | starch, approx. 0.17 g/L |
|---|---|
| Buffer: | Citrate, approx. 0.03M |
| Iodine (I$_2$): | 0.03 g/L |
| CaCl$_2$: | 1.85 mM |
| pH: | 2.50 ± 0.05 |

-continued

| Incubation temperature: | 40° C. |
|---|---|
| Reaction time: | 23 seconds |
| Wavelength: | Lambda = 590 nm |
| Enzyme concentration: | 0.025 AFAU/mL |
| Enzyme working range: | 0.01-0.04 AFAU/mL |

Further details can be found in standard method document EB-SM-0259.02/01 available on request from Novozymes A/S, which folder is hereby incorporated by reference.

Determination of FAU-F

FAU-F Fungal Alpha-Amylase Units (Fungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M Ca$^{2+}$; and pH 5.6) dextrinizes 5260 mg starch dry substance Merck Amylum soluble.

A folder EB-SM-0009.02/01 describing this analytical method in more detail is available upon request to Novozymes A S, Denmark, which folder is hereby included by reference.

Glucoamylase and Alpha-Glucosidase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: acetate | 0.1M |
| pH: | 4.30 ± 0.05 |
| Incubation temperature: | 37° C. ± 1 |

-continued

| AMG incubation: | |
| --- | --- |
| Reaction time: | 5 minutes |
| Enzyme working range: | 0.5-4.0 AGU/mL |

| Color reaction: | |
| --- | --- |
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Determination of Protease Activity (AU)

Dimethyl casein (DMC) is hydrolyzed by the proteolytic enzyme to small peptides. The primary amino groups formed in this process react with trinitrobenzene sulphonic acid (TNBS) forming a coloured complex. This colour development is monitored in situ so the change in absorption per time unit can be calculated. This FIGURE is a measure of the reaction rate and thus of the enzyme activity.

| Reaction conditions for the DMC reaction | |
| --- | --- |
| Temperature: | 50° C. |
| pH: | 8.3 |
| Wavelength: | 405 nm |
| Reaction time: | 8 min. |
| Measuring time: | 2 min. |
| Enzyme concentration range: | 0.072-0.216 mAU/ml. |

The activity is determined relative to an enzyme standard.

The assay is further described in standard method document EB-SM-0218.02/02 available upon request from Novozymes A/S, Denmark.

EXAMPLES

Example 1

Preparation of Protease Variants and Test of Thermostability

Chemicals used were commercial products of at least reagent grade.

Strains and Plasmids:

E. coli DH12S (available from Gibco BRL) was used for yeast plasmid rescue. pJTPOOO is a S. cerevisiae and E. coli shuttle vector under the control of TPI promoter, constructed from pJC039 described in WO 01/92502, in which the Thermoascus aurantiacus M35 protease gene (WO 03/048353) has been inserted.

Saccharomyces cerevisiae YNG318 competent cells: MATa Dpep4[cir+] ura3-52, leu2-D2, his 4-539 was used for protease variants expression. It is described in J. Biol. Chem. 272(15): 9720-9727 (1997).

Media and Substrates

10× Basal solution: Yeast nitrogen base w/o amino acids (DIFCO) 66.8 g/L, succinate 100 g/i, NaOH 60 g/l.

SC-glucose: 20% glucose (i.e., a final concentration of 2%=2 g/100 mL)) 100 mL/L, 5% threonine 4 mL/L, 1% tryptophan 10 ml/1, 20% casamino acids 25 ml/1, 10× basal solution 100 ml/I. The solution is sterilized using a filter of a pore size of 0.20 micrometer. Agar (2%) and $H_2O$ (approx. 761 mL) is autoclaved together, and the separately sterilized SC-glucose solution is added to the agar solution.

YPD: Bacto peptone 20 g/l, yeast extract 10 g/L, 20% glucose 100 mL/L.

YPD+Zn: YPD+0.25 mM ZnSO4.

PEG/LiAc solution: 40% PEG4000 50 ml, 5 M Lithium Acetate 1 mL.

96 Well Zein Micro Titre Plate:

Each well contains 200 microL of 0.05-0.1% of zein (Sigma), 0.25 mM $ZnSO_4$ and 1% of agar in 20 mM sodium acetate buffer, pH 4.5.

DNA Manipulations

Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, NY; Ausubel, F. M. et al. (eds.) "Current protocols in Molecular Biology", John Wiley and Sons, 1995; Harwood, C. R. and Cutting, S. M. (Eds.).

Yeast Transformation

Yeast transformation was performed using the lithium acetate method. 0.5 microL of vector (digested by restriction endonucleases) and 1 microL of PCR fragments is mixed. The DNA mixture, 100 microL of YNG318 competent cells, and 10 microL of YEAST MAKER carrier DNA (Clontech) is added to a 12 mL polypropylene tube (Falcon 2059). Add 0.6 mL PEG/LiAc solution and mix gently. Incubate for 30 min at 30° C., and 200 rpm followed by 30 min at 42° C. (heat shock). Transfer to an eppendorf tube and centrifuge for 5 sec. Remove the supernatant and resolve in 3 mL of YPD. Incubate the cell suspension for 45 min at 200 rpm at 30° C. Pour the suspension to SC-glucose plates and incubate 30° C. for 3 days to grow colonies. Yeast total DNA are extracted by Zymoprep Yeast Plasmid Miniprep Kit (ZYMO research).

DNA Sequencing

E. coli transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

Construction of Protease Expression Vector

The Thermoascus M35 protease gene was amplified with the primer pair Prot F (SEQ ID NO: 5) and Prot R (SEQ ID NO: 6). The resulting PCR fragments were introduced into S. cerevisiae YNG318 together with the pJC039 vector (described in WO 2001/92502) digested with restriction enzymes to remove the Humicola insolens cutinase gene.

The Plasmid in yeast clones on SC-glucose plates was recovered to confirm the internal sequence and termed as pJTPOOL Construction of Yeast Library and Site-Directed Variants Library in yeast and site-directed variants were constructed by SOE PCR method (Splicing by Overlap Extension, see "PCR: A practical approach", p. 207-209, Oxford University press, eds. McPherson, Quirke, Taylor), followed by yeast in vivo recombination.

General Primers for Amplification and Sequencing

The primers AM34 (SEQ ID NO: 7) and AM35 (SEQ ID NO:8) were used to make DNA fragments containing any mutated fragments by the SOE method together with degenerated primers (AM34+Reverse primer and AM35+forward primer) or just to amplify a whole protease gene (AM34+AM35).

| PCR reaction system: | | Conditions: |
|---|---|---|
| 48.5 microL H$_2$O | 1 | 94° C. 2 min |
| 2 beads puRe Taq Ready-To-Go PCR (Amersham Biosciences) | 2 | 94° C. 30 sec |
| 0.5 microL × 2 100 pmole/microL of primers | 3 | 55° C. 30 sec |
| 0.5 microL template DNA | 4 | 72° C. 90 sec |
| | 2-4 | 25 cycles |
| | 5 | 72° C. 10 min |

DNA fragments were recovered from agarose gel by the Qiagen gel extraction Kit. The resulting purified fragments were mixed with the vector digest. The mixed solution was introduced into *Saccharomyces cerevisiae* to construct libraries or site-directed variants by in vivo recombination.

Relative Activity Assay

Yeast clones on SC-glucose were inoculated to a well of a 96-well micro titre plate containing YPD+Zn medium and cultivated at 28° C. for 3 days. The culture supernatants were applied to a 96-well zein micro titer plate and incubated at at least 2 temperatures (ex., 70° C. and 80° C.) for more than 4 hours or overnight. The turbidity of zein in the plate was measured as A630 and the relative activity (higher/lower temperatures) was determined as an indicator of thermoactivity improvement. The clones with higher relative activity than the parental variant were selected and the sequence was determined.

Remaining Activity Assay

Yeast clones on SC-glucose were inoculated to a well of a 96-well micro titre plate and cultivated at 28° C. for 3 days. Protease activity was measured at 65° C. using azo-casein (Megazyme) after incubating the culture supernatant in 20 mM sodium acetate buffer, pH 4.5, for 10 min at a certain temperature (80° C. or 84° C. with 4° C. as a reference) to determine the remaining activity. The clones with higher remaining activity than the parental variant were selected and the sequence was determined.

Azo-Casein Assay 20 microL of samples were mixed with 150 microL of substrate solution (4 ml. of 12.5% azo-casein in ethanol in 96 ml. of 20 mM sodium acetate, pH 4.5, containing 0.01% triton-100 and 0.25 mM ZnS04) and incubated for 4 hours or longer.

After adding 20 microL/well of 100% trichloroacetic acid (TCA) solution, the plate was centrifuged and 100 microL of supernatants were pipetted out to measure A440.

Expression of Protease Variants in *Aspergillus oryzae*

The constructs comprising the protease variant genes were used to construct expression vectors for *Aspergillus*. The *Aspergillus* expression vectors consist of an expression cassette based on the *Aspergillus niger* neutral amylase II promoter fused to the 35 *Aspergillus nidulans* triose phosphate isomerase non-translated leader sequence (Pna2/tpi) and the *Aspergillus niger* amyloglycosidase terminator (Tamg). Also present on the plasmid was the *Aspergillus* selective marker amdS from *Aspergillus nidulans* enabling growth on acetamide as sole nitrogen source. The expression plasmids for protease variants were transformed into *Aspergillus* as described in Lassen et al., 2001, Appl. Environ. Microbiol. 67: 4701-4707. For each of the constructs 10-20 strains were isolated, purified and cultivated in shake flasks.

Purification of Expressed Variants

1. Adjust pH of the 0.22 μm filtered fermentation sample to 4.0.
2. Put the sample on an ice bath with magnetic stirring. Add (NH$_4$)$_2$SO$_4$ in small aliquots (corresponding to approx. 2.0-2.2 M (NH$_4$)$_2$SO$_4$ not taking the volume increase into account when adding the compound).
3. After the final addition of ((NH$_4$)$_2$SO$_4$, incubate the sample on the ice bath with gentle magnetic stirring for min. 45 min.
4. Centrifugation: Hitachi himac CR20G High-Speed Refrigerated Centrifuge equipped with R20A2 rotor head, 5° C., 20,000 rpm, 30 min.
5. Dissolve the formed precipitate in 200 mL 50 mM Na-acetate pH 4.0.
6. Filter the sample by vacuum suction using a 0.22 micro m PES PLUS membrane (IWAKI).
7. Desalt/buffer-exchange the sample to 50 mM Na-acetate pH 4.0 using ultrafiltration (Vivacell 250 from Vivascience equipped with 5 kDa MWCO PES membrane) overnight in a cold room. Dilute the retentate sample to 200 ml using 50 mM Na-acetate pH 4.0. The conductivity of sample is preferably less than 5 mS/cm.
8. Load the sample onto a cation-exchange column equilibrated with 50 mM Na-acetate pH 4.0. Wash unbound sample out of the column using 3 column volumes of binding buffer (50 mM Na-acetate pH 4.0), and elute the sample using a linear gradient, 0-100% elution buffer (50 mM Na-acetate+1 M NaCl pH 4.0) in 10 column volumes.
9. The collected fractions are assayed by an endo-protease assay (cf. below) followed by standard SDS-PAGE (reducing conditions) on selected fractions. Fractions are pooled based on the endo-protease assay and SDS-PAGE.

Endo-Protease Assay

1. Protazyme OL tablet/5 ml 250 mM Na-acetate pH 5.0 is dissolved by magnetic stirring (substrate: endo-protease Protazyme AK tablet from Megazyme—cat. #PRAK 1 1/08).
2. With stirring, 250 microL of substrate solution is transferred to a 1.5 mL Eppendorf tube.
3. 25 microL of sample is added to each tube (blank is sample buffer).
4. The tubes are incubated on a Thermomixer with shaking (1000 rpm) at 50° C. for 15 minutes.
5. 250 microL of 1 M NaOH is added to each tube, followed by vortexing.
6. Centrifugation for 3 min. at 16,100×G and 25° C.
7. 200 microL of the supernatant is transferred to a MTP, and the absorbance at 590 nm is recorded.

TABLE 1

Relative Activity of protease variants. Numbering of substitution(s) starts from N-terminal of the mature peptide in amino acids 1 to 177 of SEQ ID NO: 3.

| Variant | Substitution(s) and/or deletion(s) | Remaining Activity 80° C. | 84° C. |
|---|---|---|---|
| JTP082 | ΔS5/D79L/S87P/A112P/D142L | | 53% |
| JTP091 | D79L/S87P/A112P/T124V/D142L | 43% | |
| JTP092 | ΔS5/N26R/D79L/S87P/A112P/D142L | | 60% |
| JTP095 | N26R/T46R/D79L/S87P/A112P/D142L | | 62% |
| JTP096 | T46R/D79L/S87P/T116V/D142L | | 67% |
| JTP099 | D79L/P81R/S87P/A112P/D142L | | 80% |
| JTP101 | A27K/D79L/S87P/A112P/T124V/D142L | 81% | |
| JTP116 | D79L/Y82F/S87P/A112P/T124V/D142L | 59% | |
| JTP117 | D79L/Y82F/S87P/A112P/T124V/D142L | 94% | |
| JTP127 | D79L/S87P/A112P/T124V/A126V/D142L | 53% | |

TABLE 2

Relative Activity of protease variants. Numbering of substitution(s) starts from N-terminal of the mature peptide in amino acids 1 to 177 of SEQ ID NO: 3.

| Variant | Substitutions | Relative Activity 80° C./70° C. | 85° C./70° C. |
|---|---|---|---|
| JTP050 | D79L S87P A112P D142L | 23% | 9% |
| JTP134 | D79L Y82F S87P A112P D142L | 40% | |
| JTP135 | S38T D79L S87P A112P A126V D142L | 62% | |
| JTP136 | D79L Y82F S87P A112P A126V D142L | 59% | |
| JTP137 | A27K D79L S87P A112P A126V D142L | 54% | |
| JTP145 | S49P D79L S87P A112P D142L | 59% | |
| JTP146 | S50P D79L S87P A112P D142L | 63% | |
| JTP148 | D79L S87P D104P A112P D142L | 64% | |
| JTP161 | D79L Y82F S87G A112P D142L | 30% | 12% |
| JTP180 | S70V D79L Y82F S87G Y97W A112P D142L | 52% | |
| JTP181 | D79L Y82F S87G Y97W D104P A112P D142L | 45% | |
| JTP187 | S70V D79L Y82F S87G A112P D142L | 45% | |
| JTP188 | D79L Y82F S87G D104P A112P D142L | 43% | |
| JTP189 | D79L Y82F S87G A112P A126V D142L | 46% | |
| JTP193 | Y82F S87G S70V D79L D104P A112P D142L | | 15% |
| JTP194 | Y82F S87G D79L D104P A112P A126V D142L | | 22% |
| JTP196 | A27K D79L Y82F S87G D104P A112P A126V D142L | | 18% |

TABLE 3

Relative Activity of protease variants. Numbering of substitution(s) starts from N-terminal of the mature peptide in amino acids 1 to 177 of SEQ ID NO: 3.

| Variant | Substitutions | Relative Activity 80° C./70° C. |
|---|---|---|
| JTP196 | A27K D79L Y82F S87G D104P A112P A126V D142L | 55% |
| JTP210 | A27K Y82F S87G D104P A112P A126V D142L | 36% |
| JTP211 | A27K D79L Y82F D104P A112P A126V D142L | 44% |
| JTP213 | A27K Y82F D104P A112P A126V D142L | 37% |

Example 2

Temperature Profile of Selected Protease Variants Using Purified Enzymes

Selected protease variants showing good thermostability were purified and the purified enzymes were used in a zein-BCA assay as described below. The remaining protease activity was determined at 60° C. after incubation of the enzyme at elevated temperatures as indicated for 60 min.

Zein-BCA Assay:

Zein-BCA assay was performed to detect soluble protein quantification released from zein by variant proteases at various temperatures.

Protocol:

1) Mix 10 microL of 10 micro g/mL enzyme solutions and 100 microL of 0.025% zein solution in a micro titer plate (MTP).
2) Incubate at various temperatures for 60 min.
3) Add 10 microL of 100% trichloroacetic acid (TCA) solution.
4) Centrifuge MTP at 3500 rpm for 5 min.
5) Take out 15 microL to a new MTP containing 100 microL of BOA assay solution (Pierce Cat #: 23225, BOA Protein Assay Kit).
6) Incubate for 30 min at 60° C.
7) Measure A562.

The results are shown in Table 4. All of the tested protease variants showed an improved thermostability as compared to the wild type (WT) protease.

TABLE 4

Zein-BCA assay

| WT/Variant | Sample incubated 60 min at indicated temperatures (° C.) (micro g/mL Bovine serum albumin equivalent peptide released) | | | | | | |
|---|---|---|---|---|---|---|---|
| | 60° C. | 70° C. | 75° C. | 80° C. | 85° C. | 90° C. | 95° C. |
| WT (wild-type) | 94 | 103 | 107 | 93 | 58 | 38 | |
| JTP050 (D79L + S87P + A112P + D142L) | 86 | 101 | 107 | 107 | 104 | 63 | 36 |
| JTP077 (A27K + D79L + S87P + A112P + D142L) | 82 | 94 | 107 | 105 | 99 | 56 | 31 |
| JTP118 (D79L + Y82F + S87G + D104P + A112P + D142L) | 71 | 83 | 96 | 93 | 100 | 75 | 53 |
| JTP196 (A27K + D79L + Y82F + S87G + D104P + A112P + A126V + D142L) | 87 | 99 | 103 | 106 | 117 | 90 | 38 |

Example 3

Determination of Relative Activity for Proteases Using Azo Casein Assay 20 microL of samples containing approx. 0.01 mg/ml were mixed with 150 microL of substrate solution (4 mL of 12.5% azo-casein in ethanol in 96 m of 20 mM sodium acetate, pH 4.5, containing 0.01% triton-100 and 0.25 mM ZnSO$_4$) and incubated for 5 hours at 70° C. and 80° C.

After adding 20 microL/well of 100% trichloroacetic acid (TCA) solution, the plate was centrifuged and 80 microL of supernatants were pipetted out to measure A440.

| Sample name | Relative activity 80° C./70° C. |
|---|---|
| Protease RH | 34% |
| Protease TF | 106% |
| Protease OX | 19% |
| Protease PF | 154% |

Example 4

Extracting Oil Using Protease and Phospholipase

The purpose of this experiment was to extract oil using a combination of MG Prot 3 and Phospholipase PL99.

Method

Fermentation: Industrially mash liquefied with Avantec™ (alpha-amylase product available from Novozymes) was stored frozen. Two liters of mash were thawed for approximately 2 hours prior to starting this study. The dry solids (DS) content of the mash was measured on a Mettler-Toledo moisture balance, with a resulting value of 32.88% DS. The mash was prepared to 500 ppm urea and 3 ppm penicillin using solutions of 200 g/L urea and 1 g/L penicillin, respectively, and adjusted to pH 5 using 40% v/v H$_2$SO$_4$. Approximately 25 g of prepared mash was pipetted into 48 pre-weighed 50 mL centrifuge tubes, which had holes drilled in the top.

Red Star™ yeast was rehydrated, with 2.75 g of yeast placed in 50 mL of 32° C. tap water for 30 minutes. While the yeast soaked, each mash sample was dosed with diluted Spirizyme Achieve™ (glucoamylase product available from Novozymes) (0.076 AGU/μL) to an enzyme concentration of 0.600 AGU/g DS, as calculated by the following equation $$Enz.\ doze\ (ml) = \frac{Final\ enz.\ dose\ (mg\ EP/g\ DS) \times Slurry\ weight\ (g) \times Solid\ content\ (\%\ DS)}{Conc.\ enzyme\ (mg\ EP/ml)}$$

The set of 48 tubes consisted of the following 16 treatments. In summary, there were only 2 treatments repeated multiple times to yield high oil quantity.

The protease used was the protease MG Prot 3, a protease having the amino acid sequence set out in SEQ ID NO: 14 herein. The phospholipase used (PL99) is derived from *Kionochaeta*. The amino acid sequence of the phospholipase PL99 is set out in SEQ ID NO: 15 herein.

TABLE 9

Treatments Tested

| Tube | Spirizyme™ Achieve | Protease | Protease Dose | Phospholipase | Phospholipase Dose |
|---|---|---|---|---|---|
| 1 | 0.6 AGU/gDS | MG Prot 3 | 5 μg/gDS | | |
| 2 | 0.6 AGU/gDS | MG Prot 3 | 5 μg/gDS | | |
| 3 | 0.6 AGU/gDS | MG Prot 3 | 5 μg/gDS | | |
| 4 | 0.6 AGU/gDS | MG Prot 3 | 5 μg/gDS | | |
| 5 | 0.6 AGU/gDS | MG Prot 3 | 5 μg/gDS | | |
| 6 | 0.6 AGU/gDS | MG Prot 3 | 5 μg/gDS | | |
| 7 | 0.6 AGU/gDS | MG Prot 3 | 5 μg/gDS | | |
| 8 | 0.6 AGU/gDS | MG Prot 3 | 5 μg/gDS | | |
| 9 | 0.6 AGU/gDS | MG Prot 3 | 5 μg/gDS | PL99 | 5 μg/gDS |
| 10 | 0.6 AGU/gDS | MG Prot 3 | 5 μg/gDS | PL99 | 5 μg/gDS |
| 11 | 0.6 AGU/gDS | MG Prot 3 | 5 μg/gDS | PL99 | 5 μg/gDS |
| 12 | 0.6 AGU/gDS | MG Prot 3 | 5 μg/gDS | PL99 | 5 μg/gDS |
| 13 | 0.6 AGU/gDS | MG Prot 3 | 5 μg/gDS | PL99 | 5 μg/gDS |
| 14 | 0.6 AGU/gDS | MG Prot 3 | 5 μg/gDS | PL99 | 5 μg/gDS |
| 15 | 0.6 AGU/gDS | MG Prot 3 | 5 μg/gDS | PL99 | 5 μg/gDS |
| 16 | 0.6 AGU/gDS | MG Prot 3 | 5 μg/gDS | PL99 | 5 μg/gDS |

Water was dosed into each sample such that the total added volume of enzyme and water was 195 μL/25 g sample. All samples were dosed with 250 μL of rehydrated yeast solution and vortexed. Each sample was weighed when all samples had been dosed. The samples were placed in a shaking water bath set at 32° C. for 70 hours. Each sample was weighed after 70 hours of fermentation.

Distillation: A BCichi Multivapor evaporation system was used for all distillations. The unit distilled 24 samples at a time. The parameters used are shown in the following table. Tubes were weighed after distillation and weight lost during distillation was replaced with DI water. Tubes were weighed again after water addition.

| Time | 80 min |
|---|---|
| Temperature | 75° C. |
| Vacuum | 200-153 mBar (40 min) |
| | 153-148 mBar (40 min) |
| RPM | 8 |

Oil Extraction: Hexane was added to each sample at a dose of 0.125 mL hexane/1 g starting material. Each tube was covered in Dura-seal to prevent sample leakage, and mixed thoroughly. Tubes were centrifuged at 3,000×g for 10 minutes in an Avanti JE Series centrifuge with JS-5.3 rotor. After centrifugation, the oil/hexane layer (supernatant) was removed using a positive displacement pipette, transferred to a 50 ml volumetric flask. Tubes labelled 1-24 were added to the same flask (A) and tubes labelled 25-48 were added together in a second flask (B). After all the oil/hexane layers were extracted off, each treatment (+/−PL) was run on a Büchi Multivapor for about 5 minutes to evaporate the majority of the hexane layer off. The two oil samples were then poured into 50 ml tubes and left over the weekend for the rest of the hexane to evaporate off before testing.

| | Tube (A) (without PL) | Tube (B) (with PL) |
|---|---|---|
| Moisture (%) | 2.03 | 1.53 |
| Insolubles (%) | 0.14 | n.d. |
| Free fatty acid (%) | 8.92 | 9.59 |

Example 5

Extracting Oil Using Protease and Phospholipase

The purpose of this experiment is to extract oil using a combination of a protease (Protease OX) and three different phospholipases (PL99, PL100 and P101).

Method

Fermentation: Industrially mash liquefied with Avantec™ (alpha-amylase product available from Novozymes) was stored frozen. One liter of mash was thawed for approximately 2 hours prior to starting this study. The dry solids content of the mash was measured on a Mettler-Toledo moisture balance, with a resulting value of 32.17% DS. The mash was prepared to 500 ppm urea and 3 mg/L penicillin using solutions of 200 g/L urea and 1 g/L penicillin, respectively, and adjusted to pH 5 using 40% v/v H2SO4. Approximately 35 g of each prepared mash was pipetted into each of 24 pre-weighed 50 mL centrifuge tubes, which had holes drilled in the top.

The protease used was the Protease OX, a protease derived from *Thermoascus aurantiacus* having the amino acid sequence set out in SEQ ID NO: 3 herein. Three phospholipases were used (PL99, PL100 and PL1). Phospholipase PL99 is from Kionochaeata sp. and has the amino acid sequence as set out herein as SEQ ID NO: 15. Phospholipase PL100 is from *Penicillium emersonii* and has the amino acid sequence as set out herein as SEQ ID NO: 16. Phospholipase PL100 is from *Bacillus thuringiensis* and has the amino acid sequence as set out herein as SEQ ID NO: 17.

Red Star™ yeast was rehydrated, with 2.75 g of yeast placed in 50 mL of 32° C. tap water for 30 minutes.

TABLE

Treatments tested

| Treatment | Protease | Protease Dose (µg/gDS) | PL | Units (µg/gDS) | Spirizyme Excel XHS (AGU/gDS) |
|---|---|---|---|---|---|
| 1 | None | 0 | none | 0 | 0.6 |
| 2 | None | 0 | PL99 | 100 | 0.6 |
| 3 | None | 0 | PL100 | 100 | 0.6 |
| 4 | None | 0 | PL101 | 100 | 0.6 |
| 5 | Protease OX | 5 | none | 0 | 0.6 |
| 6 | Protease OX | 5 | PL99 | 100 | 0.6 |
| 7 | Protease OX | 5 | PL100 | 100 | 0.6 |
| 8 | Protease OX | 5 | PL101 | 100 | 0.6 |

TABLE

Enzymes

| Name | Stock conc. | Units | Dilution factor | Experiment conc. | Units |
|---|---|---|---|---|---|
| Spirizyme Excel ™ XHS | 1234.2 | AGU/g | 12.40 | 99.56 | AGU/g |
| Protease OX (Batch 10) | 25.25 | mg/g | 24.79 | 1.02 | ug/ul |
| PL99 | 5.5 | mg/ml | 1.00 | 5.50 | ug/ul |
| PL100 | 24 | mg/ml | 1.00 | 24.00 | ug/ul |
| PL101 | 2 | mg/ml | 1.00 | 2.00 | ug/ul |

Enzyme doses were calculated via the following equation:

$$\text{Enz. doze (ml)} = \frac{\text{Final } enz. \text{ dose}(AGU/g\ DS) \times \text{Mash weight (g)} \times \text{Solid content (\% } DS)}{\text{Conc. enzyme (mg } AGU/\text{ml})}$$

TABLE 12

Enzyme Dosing

| Treatment (protease, phospholipase) (dose µg/g DS) | Sample # | Spirizyme Excel (µL) | Protease (µL) | PL (µL) | H$_2$O (µL) | Total to add (µL) | Yeast (µL) |
|---|---|---|---|---|---|---|---|
| 1 None, 0.0 | 1 | 70.9 | 0.0 | 0.0 | 639.9 | 256.06 | 350 |
| 1 | 2 | 70.0 | 0.0 | 0.0 | 627.6 | 252.88 | 350 |

TABLE 12-continued

Enzyme Dosing

| Treatment (protease, phospholipase) (dose µg/g DS) | Sample # | Spirizyme Excel (µL) | Protease (µL) | PL (µL) | H₂O (µL) | Total to add (µL) | Yeast (µL) |
|---|---|---|---|---|---|---|---|
| 1 | 3 | 69.6 | 0.0 | 0.0 | 622.0 | 251.43 | 350 |
| 2 None, PL99 100 | 4 | 70.7 | 0.0 | 213.4 | 423.8 | 255.34 | 350 |
| 2 | 5 | 70.9 | 0.0 | 213.9 | 425.7 | 255.99 | 350 |
| 2 | 6 | 70.9 | 0.0 | 213.9 | 425.7 | 255.99 | 350 |
| 3 None, PL 100 | 7 | 71.2 | 0.0 | 49.2 | 595.0 | 257.19 | 350 |
| 3 100 | 8 | 71.2 | 0.0 | 49.2 | 594.7 | 257.12 | 350 |
| 3 | 9 | 70.9 | 0.0 | 49.0 | 590.0 | 255.82 | 350 |
| 4 None, PL101 | 10 | 71.2 | 0.0 | 590.3 | 52.8 | 256.89 | 350 |
| 4 100 | 11 | 71.2 | 0.0 | 590.8 | 53.2 | 257.11 | 350 |
| 4 | 12 | 69.8 | 0.0 | 579.0 | 45.1 | 251.99 | 350 |
| 5 Protease OX, | 13 | 69.9 | 57.0 | 0.0 | 605.0 | 251.47 | 350 |
| 5 5.0 | 14 | 70.4 | 57.3 | 0.0 | 611.4 | 256.81 | 350 |
| 5 | 15 | 68.3 | 55.6 | 0.0 | 582.6 | 249.60 | 350 |
| 6 Protease OX, | 16 | 69.7 | 56.7 | 210.1 | 391.2 | 255.79 | 350 |
| 6 PL99 100 | 17 | 71.1 | 57.9 | 214.6 | 407.0 | 254.25 | 350 |
| 6 | 18 | 69.1 | 56.3 | 208.6 | 385.7 | 253.11 | 350 |
| 7 Protease OX, | 19 | 70.8 | 57.7 | 49.0 | 568.7 | 253.31 | 350 |
| 7 PL100 100 | 20 | 70.4 | 57.4 | 48.7 | 563.2 | 253.55 | 350 |
| 7 | 21 | 70.1 | 57.1 | 48.5 | 559.1 | 253.95 | 350 |
| 8 Protease OX, | 22 | 70.2 | 57.2 | 582.1 | 26.2 | 0.00 | 350 |
| 8 PL101 100 | 23 | 70.2 | 57.2 | 582.6 | 26.6 | 0.00 | 350 |
| 8 | 24 | 70.3 | 57.3 | 583.5 | 27.2 | 0.00 | 350 |

Water was dosed into each sample such that the total added volume of enzyme and water was 725 and 750 µL/35 g sample. All samples were dosed with 350 µL of rehydrated yeast solution and vortexed. Each sample was weighed when all samples had been dosed. The samples were placed in a shaking incubator set at 32° C. for 70 hours. Each sample was weighed after 70 hours of fermentation to monitor ethanol production.

Distillation: A Büchi Multivapor evaporation system was used for all distillations. The unit distilled 12 samples at a time. The parameters used are shown in the table below. Tubes were weighed after distillation and weight lost during distillation was replaced with DI water. Tubes were weighed again after water addition.

| Time | 80 min |
|---|---|
| Temperature | 75° C. |
| Vacuum | 200-153 mBar (40 min) 153-148 mBar (40 min) |
| RPM | 8 |

Oil Extraction: Hexane was added to each sample at a dose of 0.125 mL hexane/1 g starting material. Each tube was covered in Dura-seal to prevent sample leakage, and mixed thoroughly. Tubes were centrifuged at 3,000×g for 10 minutes in an Avanti JE Series centrifuge with JS-5.3 rotor. After centrifugation, the oil/hexane layer (supernatant) was removed using a positive displacement pipette, transferred to 15 mL screw-cap tubes. Tubes were allowed stand open in a chemical hood so that the hexane would be evaporated. Tubes were filmed, capped, and tested.

| Protease | PLC | | HPLC DG % | ICP P (ppm) | NMR P (ppm) |
|---|---|---|---|---|---|
| None | None | Sample 1 | 1.7 | 52 | 52 |
| None | PL99 | Sample 2 | 6.2 | 35 | 52 |
| None | PL100 | Sample 3 | 2.8 | 28 | 34 |
| None | PL101 | Sample 4 | 3.3 | 31 | 41 |
| Protease OX | None | Sample 5 | 2.1 | 20 | 43 |
| Protease OX | PL99 | Sample 6 | 6.4 | 48 | 36 |
| Protease OX | PL100 | Sample 7 | 3.2 | 38 | 0 |
| Protease OX | PL101 | Sample 8 | 3.6 | 35 | 57 |

Conclusion

Percent diglyceride (DG) increased with the use of phospholipase-C, with phospholipase PL99 performing the best.

Example 6

The purpose of this experiment is to extract oil using Protease OX alone and a Protease OX in combination with three different doses of a phospholipase (PL99) so that it may be evaluated for oil quality (degumming).

Method

Fermentation: Industrially mash liquefied with Avantec™ (alpha-amylase product available from Novozymes) was stored frozen. One liter of mash was thawed for approximately 2 hours prior to starting this study. The dry solids content of the mash was measured on a Mettler-Toledo moisture balance, with a resulting value of 32.04% DS. The mash was prepared to 500 ppm urea and 3 mg/L penicillin using solutions of 200 g/L urea and 1 g/L penicillin, respectively, and adjusted to pH 5 using 40% v/v $H_2SO_4$. Approximately 35 g of each prepared mash was pipetted into each of 24 pre-weighed 50 mL centrifuge tubes, which had holes drilled in the top.

The protease used was the Protease OX, a thermostable protease derived from *Thermoascus aurantiacus* having the amino acid sequence set out in SEQ ID NO: 3 herein. Phospholipase PL99 is from *Kionochaeata sp.* and has the amino acid sequence as set out herein as SEQ ID NO: 15.

Red Star™ yeast was rehydrated, with 2.75 g of yeast placed in 50 mL of 32° C. tap water for 30 minutes. While the yeast soaked, each mash sample was dosed with diluted Spirizyme Excel™ XHS (glucoamylase product available from Novozymes) (0.07 AGU/µL) to an enzyme concentration of 0.600 AGU/g DS, as calculated by the following equation.

Enz. dose (ml)=Final enz. dose (AGU/gDS)×Mash weight (g)×Solid content (% DS)/Conc. enzyme (mg AGU/ml)

Each set of 6 tubes consisted of the following 4 treatments:

TABLE

Treatments tested

| Treatment | Protease | Dose | Units | PL | Dose | Units | GA | Dose | Units |
|---|---|---|---|---|---|---|---|---|---|
| 1 | Protease OX | 5 | µg/gDS | none | 0.000 | µg/gDS | Sp. Excel | 0.6 | AGU/gDS |
| 2 | Protease OX | 5 | µg/gDS | PL99 | 1 | µg/gDS | Sp. Excel | 0.6 | AGU/gDS |
| 3 | Protease OX | 5 | µg/gDS | PL99 | 5 | µg/gDS | Sp. Excel | 0.6 | AGU/gDS |
| 4 | Protease OX | 5 | µg/gDS | PL99 | 100 | µg/gDS | Sp. Excel | 0.6 | AGU/gDS |

Water was dosed into each sample such that the total added volume of enzyme and water was 400 µL/25 g sample. All samples were dosed with 350 µL of rehydrated yeast solution and vortexed. Each sample was weighed when all samples had been dosed. The samples were placed in a shaking incubator set at 32° C. for 70 hours. Each sample was weighed after 70 hours of fermentation to monitor ethanol production.

Distillation: A Büchi Multivapor evaporation system was used for all distillations. The unit distilled 24 samples at a time. The parameters used are shown in the following table. Tubes were weighed after distillation and weight lost during distillation was replaced with DI water. Tubes were weighed again after water addition.

| Time | 80 min |
|---|---|
| Temperature | 75° C. |
| Vacuum | 200-153 mBar (40 min) 153-148 mBar (40 min) |
| RPM | 8 |

Oil Extraction: Hexane was added to each sample at a dose of 0.125 mL hexane/1 g starting material. Each tube was covered in Dura-seal to prevent sample leakage, and mixed thoroughly. Tubes were centrifuged at 3,000×g for 10 minutes in an Avanti JE Series centrifuge with JS-5.3 rotor. After centrifugation, the oil/hexane layer (supernatant) was removed using a positive displacement pipette, transferred to a 5 mL vial. Vials were wrapped, sealed, and tested.

| Sample ID | 1.3 DG (DG % content) | 1.2 DG (DG % content) | Total DG (DG % content) |
|---|---|---|---|
| 1 | 1.67 | 0.73 | 2.39 |
| 2 | 1.69 | 0.77 | 2.47 |
| 3 | 1.67 | 0.72 | 2.39 |
| 4 | 1.69 | 0.76 | 2.45 |
| 5 | 1.70 | 0.76 | 2.46 |
| 6 | 1.75 | 0.77 | 2.51 |
| 7 | 2.10 | 1.24 | 3.33 |
| 8 | 2.07 | 1.22 | 3.29 |
| 9 | 2.03 | 1.19 | 3.22 |
| 10 | 2.07 | 1.23 | 3.29 |
| 11 | 2.04 | 1.21 | 3.25 |
| 12 | 2.06 | 1.24 | 3.30 |
| 13 | 2.28 | 1.51 | 3.78 |
| 14 | 2.22 | 1.49 | 3.72 |
| 15 | 2.23 | 1.48 | 3.71 |
| 16 | 2.28 | 1.52 | 3.80 |
| 17 | 2.21 | 1.48 | 3.69 |
| 18 | 2.28 | 1.50 | 3.79 |
| 19 | 3.25 | 2.82 | 6.08 |
| 20 | 3.31 | 2.80 | 6.10 |
| 21 | 3.32 | 2.82 | 6.14 |
| 22 | 3.29 | 2.82 | 6.11 |
| 23 | 3.34 | 2.90 | 6.24 |
| 24 | 3.43 | 3.00 | 6.43 |

Conclusions: Treatments 2 and 3 (5 µg Protease OX with 1 and 5 µg of PLC, respectively) yielded similar results in % diglyceride (DG) content. 1.3 DG refers to a diglyceride with fatty acid moieties on the first and third carbons of the glycerol backbone. 1.2 DG refers to a diglyceride with fatty acid moieties on the first and second carbons of the glycerol backbone. The diglycerides are formed by the hydrolysis of a phospholipid by a phospholipase. Treatment 4 (5 µg Protease OX with 100 µg of PLC) nearly doubled the % DG.

The invention claimed is:

1. A process of recovering oil, comprising
   (a) converting a starch-containing material into dextrins with an alpha-amylase;
   (b) saccharifying the dextrins using a carbohydrate source generating enzyme to form a sugar;
   (c) fermenting the sugar in a fermentation medium into a fermentation product using a fermenting organism;
   (d) recovering the fermentation product to form a whole stillage;
   (e) separating the whole stillage into thin stillage and wet cake;
   (e') optionally concentrating the thin stillage into syrup;
   (f) recovering oil from the thin stillage and/or optionally the syrup, wherein a protease and a phospholipase are present and/or added during steps (a) to (c);
   wherein the protease present and/or added in steps (a) to (c) is a protease having the amino acid sequence set forth in SEQ ID NO: 9 or a protease having at least 85% identity to SEQ ID NO: 9 and having protease activity; and
   wherein the phospholipase present and/or added in steps (a) to (c) is:
   (i) the phospholipase shown in SEQ ID NO: 15 or one having a sequence identity thereto of at least 90% and having phospholipase activity;
   (ii) the phospholipase shown in SEQ ID NO: 16 or one having a sequence identity thereto of at least 90% and having phospholipase activity; or
   (iii) the phospholipase shown in SEQ ID NO: 17 or one having a sequence identity thereto of at least 90% and having phospholipase activity.

2. The process of claim 1, wherein the protease is added together with the alpha-amylase in step (a).

3. The process of claim 1, wherein the protease and the phospholipase are present and/or added during steps (b) and/or (c).

4. The process of claim 3, wherein the protease and the phospholipase are added sequentially.

5. The process of claim 3, wherein the protease and the phospholipase are added simultaneously.

6. The process of claim 1, wherein the step (a) is performed at a temperature above the initial gelatinization temperature.

7. The process of claim 1, wherein a protease is added in step (a) carried out above the initial gelatinization temperature.

8. The process of claim 1, wherein the step (a) is performed a temperature below the initial gelatinization temperature.

9. The process of claim 1, wherein saccharification step (b) and fermentation step (c) are carried out simultaneously.

10. The process of claim 1, wherein saccharification step (b) and fermentation step (c) are carried out sequentially.

11. The process of claim 1, wherein steps (a), (b) and (c) are carried out simultaneously at a temperature below the initial gelatinization temperature.

12. The process of claim 1, wherein steps (a), (b) and (c) are carried out sequentially at a temperature below the initial gelatinization temperature.

* * * * *